United States Patent
Moses

(10) Patent No.: US 10,265,063 B1
(45) Date of Patent: Apr. 23, 2019

(54) DEEP CAVITY SUTURE DEVICE

(71) Applicant: Keith Brian Moses, Seatac, WA (US)

(72) Inventor: Keith Brian Moses, Seatac, WA (US)

(*) Notice: Subject to any disclaimer, the term of this patent is extended or adjusted under 35 U.S.C. 154(b) by 0 days.

(21) Appl. No.: 16/189,060

(22) Filed: Nov. 13, 2018

Related U.S. Application Data

(60) Provisional application No. 62/614,457, filed on Jan. 7, 2018.

(51) Int. Cl.
*A61B 17/04* (2006.01)
*A61B 17/06* (2006.01)
*A61B 17/00* (2006.01)
*A61B 17/062* (2006.01)

(52) U.S. Cl.
CPC ...... *A61B 17/0469* (2013.01); *A61B 17/0482* (2013.01); *A61B 17/06166* (2013.01); *A61B 17/0401* (2013.01); *A61B 17/062* (2013.01); *A61B 2017/00663* (2013.01); *A61B 2017/0474* (2013.01); *A61B 2017/0479* (2013.01)

(58) Field of Classification Search
CPC ............ A61B 17/0469; A61B 17/0625; A61B 17/2909; A61B 17/0491
See application file for complete search history.

(56) References Cited

U.S. PATENT DOCUMENTS

| | | |
|---|---|---|
| 3,137,276 A | 6/1964 | Weisser |
| 3,289,638 A | 12/1966 | Levolin |
| 5,178,265 A | 1/1993 | Sepke |
| 5,263,786 A | 11/1993 | Kageyama |
| 5,478,344 A * | 12/1995 | Stone ............... A61B 17/0469 206/339 |
| 5,522,820 A * | 6/1996 | Caspari ............ A61B 17/0625 606/139 |
| 5,674,229 A * | 10/1997 | Tovey ............... A61B 17/0469 606/139 |
| 5,728,107 A | 3/1998 | Zlock et al. |
| 6,126,666 A * | 10/2000 | Trapp ............... A61B 17/0469 206/339 |
| 6,719,763 B2 | 4/2004 | Chung et al. |
| 7,879,046 B2 * | 2/2011 | Weinert ............ A61B 17/0469 606/139 |
| 8,465,505 B2 * | 6/2013 | Murillo ............ A61B 17/0469 606/144 |
| 8,628,545 B2 * | 1/2014 | Cabrera ............ A61B 17/0469 606/144 |

(Continued)

*Primary Examiner* — Phong Son H Dang
(74) *Attorney, Agent, or Firm* — Stephen E. Zweig

(57) ABSTRACT

An apparatus for suturing tissue. The apparatus comprises shaft mounted jaw mechanism and a housing (containing mechanical components) mounted on the proximal portion of the shaft. The jaw mechanism comprises two pivoting jaws, each with reversibly lockable needle end openings, each configured to receive and exchange a curved needle and attached suture between the jaws in response to force applied to control mechanisms on the housing. The jaw mechanisms are controlled by locking rods and a jaw open-shut control rod that extends between the jaws and the housing. The housing contains spring loaded click cam mechanisms, often comprising a dual hollow cylindrical cam inner piston cam arrangement. The apparatus is configured so that a human operator, exerting force on the same control mechanism, can both open and shut the jaws and cause the needle to be exchanged between jaws.

20 Claims, 21 Drawing Sheets

(56) References Cited

U.S. PATENT DOCUMENTS

| | | | |
|---|---|---|---|
| 8,864,776 B2 * | 10/2014 | Bogart | A61B 17/06004 |
| | | | 606/144 |
| 8,968,340 B2 * | 3/2015 | Chowaniec | A61B 17/0469 |
| | | | 606/144 |
| 9,675,340 B2 * | 6/2017 | Sniffin | A61B 17/06066 |
| 9,907,550 B2 * | 3/2018 | Sniffin | A61B 17/0469 |
| 2006/0036232 A1 * | 2/2006 | Primavera | A61B 17/0469 |
| | | | 604/411 |

* cited by examiner

Tissue suture

Cutting jaw positioned close to the knot

DEEP CAVITY SUTURE DEVICE

CROSS REFERENCE TO RELATED APPLICATIONS

This application claims the priority benefit of U.S. provisional patent application 62/614,457, filed January 2018, the entire contents of which are incorporated herein by reference.

BACKGROUND OF THE INVENTION

Field of the Invention

This invention is in the field of surgical tools, such as suturing devices configured for endoscopic and other deep cavity suturing applications.

Description of the Related Art

One of the most common surgical procedures is suturing, in which two or more sections of tissue are stitched together, most classically using sterilized needle and suture thread techniques, often with the aid of various surgical knots. A wide variety of various types of needles and thread materials have been used for these techniques.

As surgical technology and understanding has advanced, the advantages of minimally invasive surgery, which attempts to reduce the amount of damage to the body by using ever smaller incisions, have become apparent. In particular, laparoscopic and natural orifice techniques have become increasingly popular. As this popularity has increased, the need for improved techniques to create sutures in small tight spaces has become apparent. As anyone who has ever attempted to sew using conventional needles and thread can attest, absent some sort of specialized tools, human hands alone are inadequate to the task because they simply take up too much space.

As a result, there has been a considerable amount of medical interest in the development of specialized suturing devices that enable sutures to be performed in small spaces, such as various laparoscopic and endoscopic surgical situations.

For example, Zlock et. al., U.S. Pat. No. 5,728,107, taught a "surgical suturing apparatus with loading mechanism", the contents of which are incorporated herein by reference. Variations on this type of device are presently marketed by Medtronic minimally invasive therapies group, (formerly Coviden LLC) as the Endo Stitch™ suturing device. Similarly, Sydney Sheung Chee Chung et. al., in U.S. Pat. No. 6,719,763, taught an "Endoscopic suturing device". This was an Endoscopic suturing device with a dedicated endoscope with detachably arrange needles at the distal end of the endoscope. Variations on this type of device are presently produced by Apollo Endosurgery as the OverStitch™ endoscopic suturing instrument. The entire contents of U.S. Pat. No. 6,719,763 are also incorporated herein by reference.

Prior art Zlock type devices, shown in FIG. 1A (1), generally consist of an elongated body portion (3), first and second jaws (4,5) extending from the distal portion of this elongated body. Two armed handle (2) on housing (61) is used to open and close the jaws. A needle (14) is reversibly attached to either jaw (4) or jaw 5, such as by way of recess (15). The movement of the needle from jaw (4) to jaw (5) is controlled by a side arm (25) (and a wheel, not shown) that is separate from the two armed handle used to open and close the jaws.

OverStitch™ type devices generally include an endoscope, a curved needle detachably arranged at the distal end portion of or integrally embedded in the endoscope for suturing tissue with the curved needle, and a drive arranged on the endoscope and operating the curved needle.

Rotating cam (click-cam) devices: Push button type "click cam" devices used to extend and retract ball point pen tips are known in the art. Such devices include Weisser, U.S. Pat. No. 3,137,276; Levoin, U.S. Pat. No. 3,298,638; Kageyama U.S. Pat. No. 5,263,786; and other type devices included in classification B43K24/084. Alternative type rotating cam mechanisms are taught by Sepke, U.S. Pat. No. 5,178,265. The entire contents of U.S. Pat. Nos. 3,137,276; 3,298,638; 5,263,786, and 5,178,265 are incorporated herein by reference.

BRIEF SUMMARY OF THE INVENTION

The invention is based, in part, on the insight that one problem with prior art devices, such as the art of Zlock, and the Endo Stitch™ device, is that the process of opening and shutting the jaws (Zlock uses two-armed handle 2) and transferring the needle from one jaw to the other jaw (Zlock uses separate side arm 25) typically requires the user to perform multiple mechanical operations, and often requires use of both hands to do so.

For example, the Endo Stitch™ device typically requires that to make a stitch, the operator must mechanically operate different Endo Stitch mechanical control mechanisms. For example, during suturing, these prior art devices require the user to use a first squeeze handle (2) on the Endo Stitch device's housing (61) to cause the jaw (4, 5) to close, resulting in the needle taking a first "bite" through the tissues. However, to progress further with the suture, the needle (14) must next be unlocked from a first jaw (4) on one side of the tissues and locked onto the other second jaw (5) on the other side of the tissues.

To transfer the needle from one jaw to the other, the surgeon must use a different, second mechanical control device (25) on the Endo Stitch's housing (61). This second mechanical control device (25) is located in a part of the housing (61) different from the squeeze handles (2). This second mechanical control device (25) is used to then transfer the needle from one jaw to the other jaw, and to lock the needle into position on the other jaw.

As a practical matter, since one of the surgeon's hands is often engaged with squeezing the first squeeze handle control mechanism, this often requires that the surgeon's other hand be used to on the second control mechanism to produce the unlocking/locking and needle transfer operations required to transfer the needle from one jaw to the other.

Such two-handed operations are cumbersome, and also increase the amount of skill and training required to operate the device.

Furthermore, the OverStitch™ requires cumbersome time-consuming assembly process that requires attachments proximally and distally to an Olympus only compatible dual channel endoscope. As a particular matter, are one of the surgeon's hands is often engaged with the OverStitch™ handle, mounted to the endoscope control handle, which actuates the needle driver attached at the distal end, while the other hand manages the passing of suture with the anchor exchange catheter placed in one scope channel. Additionally, a secondary scope channel (opening) is often needed to manipulate the tissue as well.

By contrast, the present invention teaches an improved and easier to use device configured with alternative mechanical mechanisms that enable the process of jaw opening and closing and needle locking and unlocking and transferring to be done with a single mechanical control device present at the same location on the housing. This streamlined single location control mechanism makes the device easier to operate and allows one-handed use if desired Thus in some embodiments, the invention may comprise an apparatus and method for suturing tissue comprising a jaw mechanism on the distal portion of a shaft, and a housing containing mechanical components on the proximal portion of the shaft. The jaw mechanism comprises two pivoting jaws, each with reversibly lockable needle end openings, each configured to receive and exchange a curved needle and attached suture between the jaws in response to force applied to control mechanisms on the housing. The jaw mechanisms are controlled by locking rods and a jaw open-shut control rod that extends between the jaws and the housing.

The housing contains at least one, and often more (e.g. two) spring loaded click cam mechanisms, often comprising a dual hollow cylindrical cam, each with an inner piston cam arrangement. This piston cam can alternatively be termed a "plunger". One piston cam being normally extended and the other being normally retracted. The apparatus is configured so that a human operator, exerting a force on the same control mechanism, can both open and shut the jaws and cause the needle to be exchanged between jaws.

DETAILED DESCRIPTION OF THE INVENTION

Figure 1A:
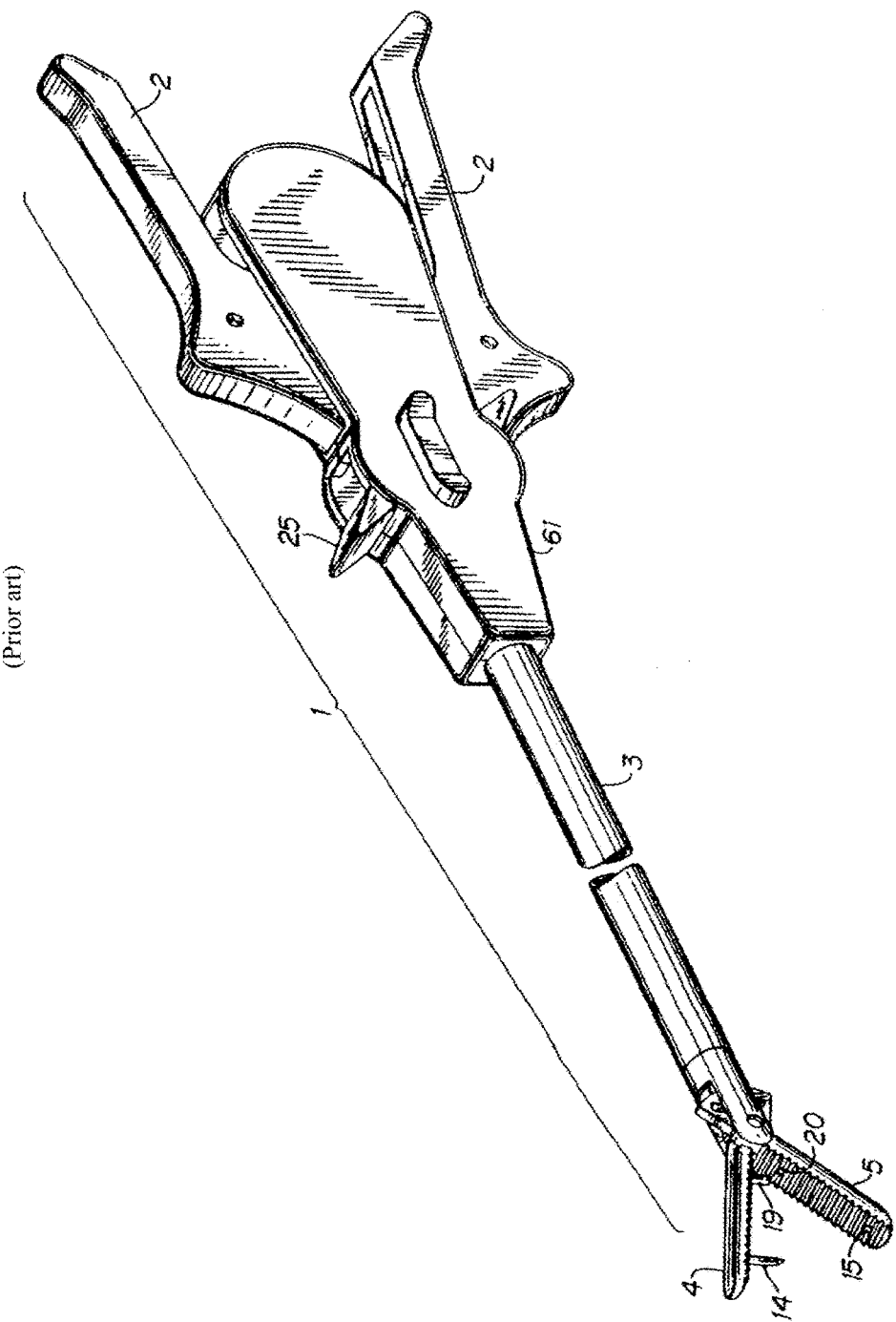
FIG. 1A shows an example of a prior art device (Zlock et. al., U.S. Pat. No. 5,728,107) showing that in the prior art device, separate controls are needed to control the opening of the jaws, as well as to control the transfer of the needle from one jaw to another jaw.
Figure 1B:
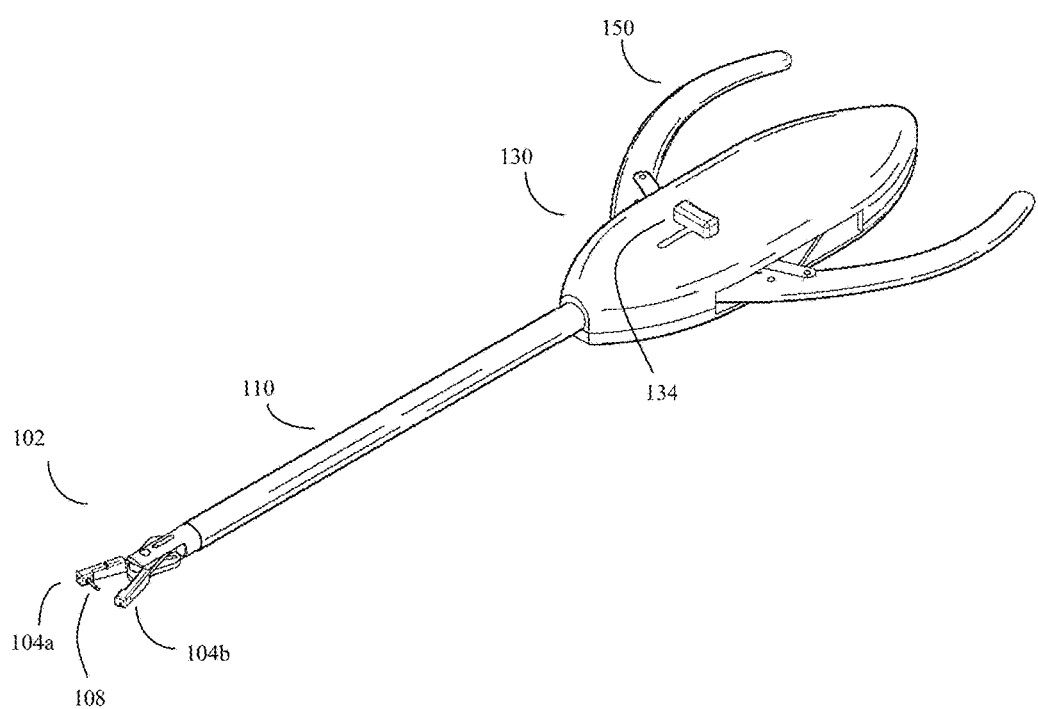
FIG. 1B shows an overall side view of one embodiment of the invention with the jaws in an open position.

FIG. 1B shows an overall side view of one embodiment of the invention with the jaws in an open position.

In some embodiments, the invention (100) may be an apparatus for operating on (suturing) tissue. This apparatus may, for example, comprise a jaw mechanism (102) comprising two pivoting jaws (104a, 104b), each jaw comprising reversibly lockable needle end openings (106a, 106b). Both of these jaws are configured to receive a curved needle (108), such that said curved needle is movable within and between reversibly lockable needle end openings.

This jaw mechanism (102) is positioned on a distal end of a substantially hollow shaft (110). According to the invention, a locking rod assembly comprising a first and second locking rod (112a, 112b) and a click cam assembly (114a, 114b) is positioned proximate to the jaw mechanism (102) and other portions of this locking rod assembly are configured to reside inside the substantially hollow shaft (110) and to be translatable (i.e. able to move) relative to the substantially hollow shaft. The device also comprises a housing (130), with optional control handles (150) which is positioned at a proximal end of the substantially hollow shaft (110).

In a preferred embodiment, these mechanical control handles form a single or same human activated control mechanism that can both open and shut the jaws and also transfer the needle from one jaw to the other.

The click cam assembly 114a, 114b, in some embodiments, comprises a pair of spring-loaded hollow cylindrical cam and piston cam arrangements, where each rotates and extends the piston (and the connected rod assemblies) to various distances during operation. This is not unlike other types of spring-loaded cams, such as certain types of pen push mechanisms. This cam action independently moves the two-rod assemblies (112a, 112b) longitudinally within the housing and the shaft. Often either the cylindrical cam rotates with respect to the piston cam, or alternatively, the piston cam may rotate with respect to the cylindrical cam.

Put alternatively, the invention's click cam system activates the rods (112a, 112b) to lock and unlock the needle when the handle is depressed all the way. The click cam system is not unlike the "push, push button" of a ballpoint pen. As you push on the pen's button, the pen slides out and locks in place. When you push again, the pen retracts into the pen housing.

This housing is configured to receive proximal portions of the first and second locking rods, and has at least one spring-loaded mechanism.

These spring-loaded mechanisms are generally configured so that they can independently move the first and second locking rods longitudinally within both the housing and the substantially hollow shaft.

The locking rod assembly and the at least one spring-loaded mechanisms are configured to automatically use the same mechanical mechanism to both open and shut the jaws, as well as to produce a locking status change in both jaw's reversibly lockable needle end openings. This locking status change will typically comprise a change from a locked to an unlocked status for one jaw, and also a change from an unlocked to a locked status for the other jaw, each jaw being in a different locking status, so that the needle may be transferred from one jaw to the other jaw.

FIG. 1 also shows a needle release override switch (134) which will be discussed shortly.

Figure 2:
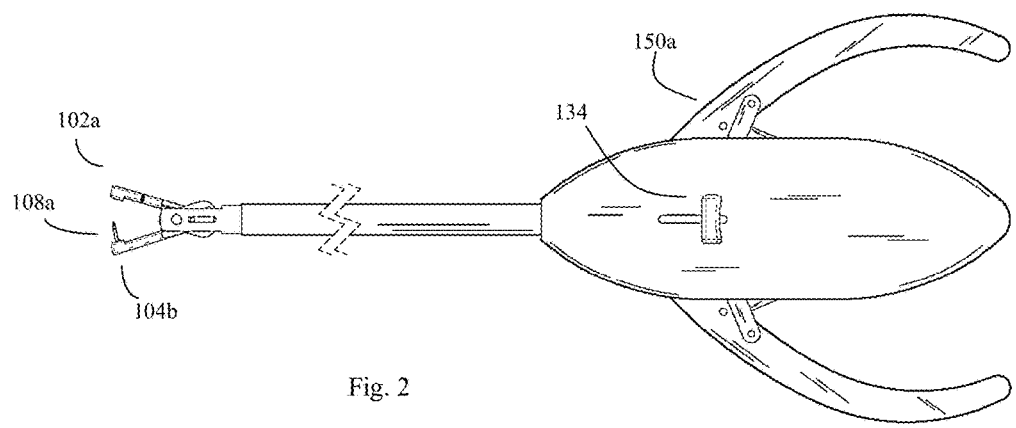
FIG. 2 shows an overhead view of the invention with the jaws and control handles in an open position. Note the position of the needle, which is affixed to the lower jaw. The suture thread is not shown.

FIG. 2 shows an overhead view of the invention with the jaws (102a) and control handles (150) in an open position. Note the position of the needle (108a), which is affixed to the lower jaw (104b). The suture thread is not shown.

Figure 3:
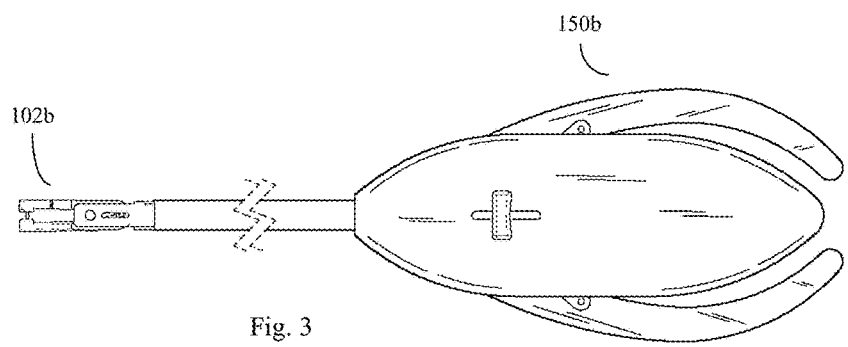
FIG. 3 shows the invention where, due to the application of hand force on the control handles, forcing the control handles shut, the invention has now configured the jaws in a closed position.

FIG. 3 shows the invention where, due to the application of hand force on the control handles (150b), forcing the control handles partially shut; the invention has now configured the jaws in a first closed position (102b).

Figure 4:
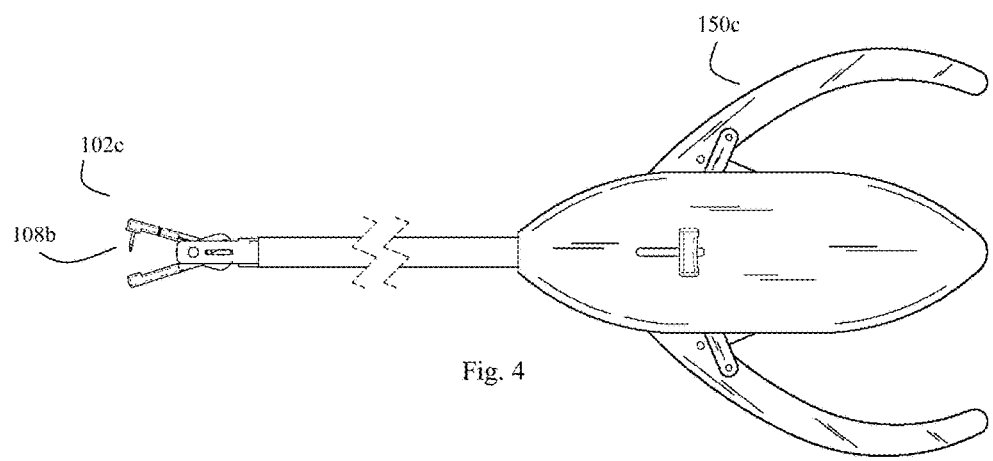
FIG. 4 shows that when the control handles are depressed and then allowed to release back into an open position, the invention now has configured the jaws again to open, but note that the needle is now affixed to the upper jaw.

FIG. 4 shows that when the control handles are depressed and then allowed to release back into an open position (150c), the invention now has configured the jaws again to open (102c), but note that the needle (108b) is now affixed to the upper jaw.

Figure 5:
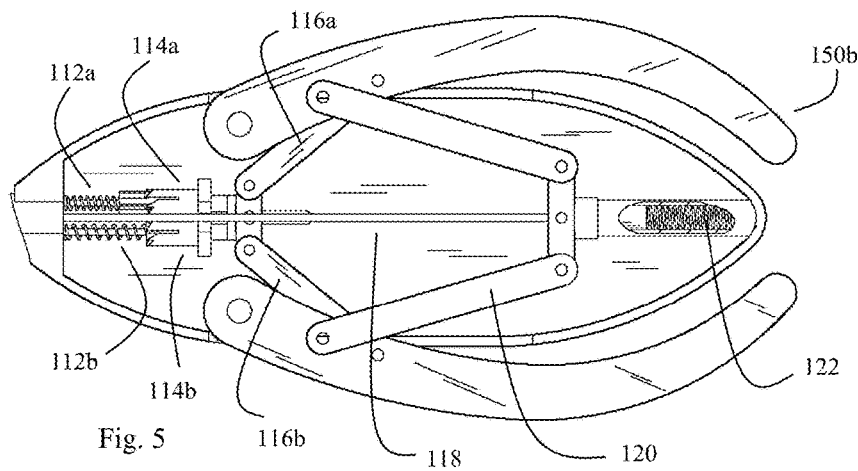
FIG. 5 shows a corresponding view of the interior of the device housing during the action previously shown in FIG. 2.

FIG. 5 shows a corresponding view of the interior of the device housing during the action previously shown in FIG. 2. FIG. 5 shows the action of the spring-loaded lever mechanisms and control handles when the control handles are squeezed to a first shut position (150b), but not fully shut.

Note that the locking rod (112b) has been moved to an extended (unlocked) position, while locking rod (112a) has been moved to a compressed (locked) position. The locking rod extends up through the hollow shaft to the jaws, which also contain hollow openings for the locking rod. When the locking rod is extended on the housing side, it is withdrawn from the hollow opening in the corresponding portion of the jaw, thus unlocking the reversibly lockable needle end opening, and releases the end of the needle (if it is present). Similarly, when the locking rod is compressed on the housing side, it enters into the hollow opening in the corresponding portion of the jaw more completely, and this locks the reversibly lockable needle end opening, and locks the end of the needle in place (if it is present).

This configuration by the time the rods reach the jaw mechanism, results in the lower jaw gripping its end of the needle because the lower jaw lockable opening is in a locked configuration. By contrast, the upper jaw has its lockable needle opening in an unlocked configuration, as was shown in FIG. 2.

Note the click cam assembly (114a, 114b) which drives the locking rods. This click cam assembly in turn, is controlled by the needle locking rod control linkages attached to the control handles (150a, b, and c).

Other mechanisms, such as the jaw open-shut control rods (118), the jaw control linkage (120), and the jaw control spring assembly (122) are used to normally keep the jaws (102) open in the absence of force applied to the control handles (150, 150b).

Figure 6:
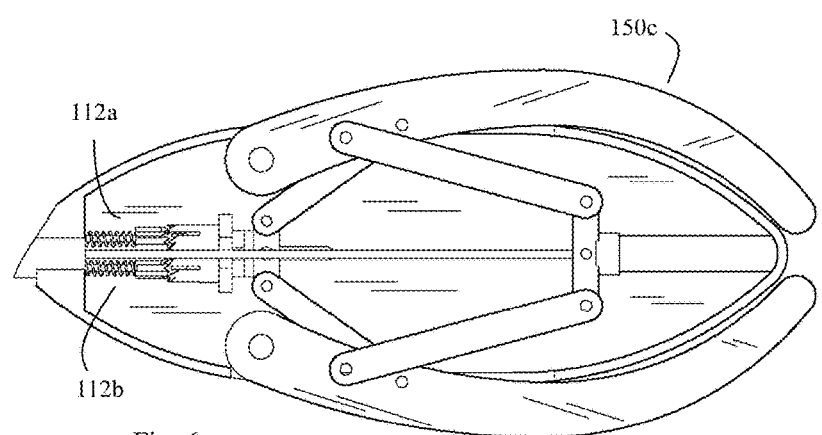
FIG. 6 shows a corresponding view of the interior of the device housing during the action previously shown in FIG. 3.

FIG. 6 shows a corresponding view of the interior of the device housing during the action previously shown in FIG. 3. FIG. 6 shows the action of the spring-loaded lever mechanisms and control handles when the control handles are squeezed to a second, fully shut position (150c). The internal device mechanism has now moved the lower locking rod (112b) to a compressed (locked) position, while the upper locking rod (112a) also continues to remain in its compressed (locked) position. Note the corresponding motion of the click cam assembly (114a, 114b) which as previously discussed, drives the locking rods (112a, 112b). As before, this click cam assembly in turn is controlled by the needle locking rod control linkages attached to the control handles (150a, b, and c). This corresponds to both lower jaw and the upper jaw holding the needle because both are in the locked configuration, as shown in FIG. 3.

Figure 7:
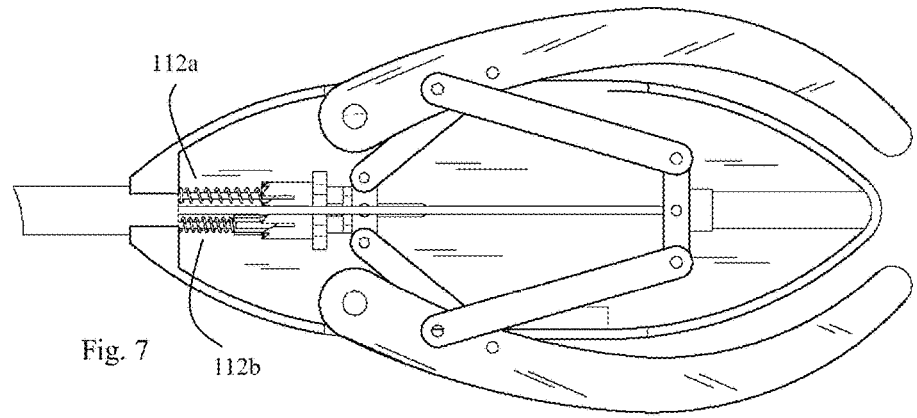
FIG. 7 shows a corresponding view of the interior of the device housing during the action previously shown in FIG. 4.

FIG. 7 shows a corresponding view of the interior of the device housing during the action previously shown in FIG. 4. FIG. 7 shows the action of the spring-loaded lever mechanisms and control handles when the control handles (150c) are now relaxed back to the original first, partially shut position. The internal device mechanisms (114a, 114b, 116a, 116b) have now moved the upper locking rod (112a) to an extended (unlocked) position. This corresponds to the lower jaw releasing its end of the needle (108b) because the lower jaw lockable opening is in an unlocked configuration. By contrast, the upper jaw is now gripping its end of the needle (108b) because its lockable needle opening is now in a locked configuration.

In some embodiments of the invention, the jaw locks and releases needle ends by using a unique spring mounted cylindrical piston cam arrangement, previously shown in overview as (114a, and 114b). This arrangement may further comprise a tandem (dual) arrangement of hollow cylindrical cams (114c, 114d), each with cam edges (114e) arranged around one outer top of the hollow cylinder (e.g. around an annular region surrounding the hollow cylinder's axis). Positioned inside each of these hollow cylindrical cams is an inner spring-loaded piston cam (114g, 114h), each with its own cam edges (114i). Upon application of a first pressure to the spring-loaded inner piston cam, the interaction between the piston cam and the cylindrical cam causes the piston cam to twist slightly and become engaged in a first position. Application of a second pressure to the spring-loaded inner piston cam causes the piston cam to twist slightly again and be engaged in a second position. The first and second positions engage the inner piston cam at various distances inside the hollow cylindrical cam, and this translates to extending or contracting the first and second locking rods (112a, 112b). Third and fourth positions can also be encoded into the cam structure as desired.

Due to the repeating cyclic nature of the cylindrical arrangement, this process can be repeated indefinitely.

Figure 7A:
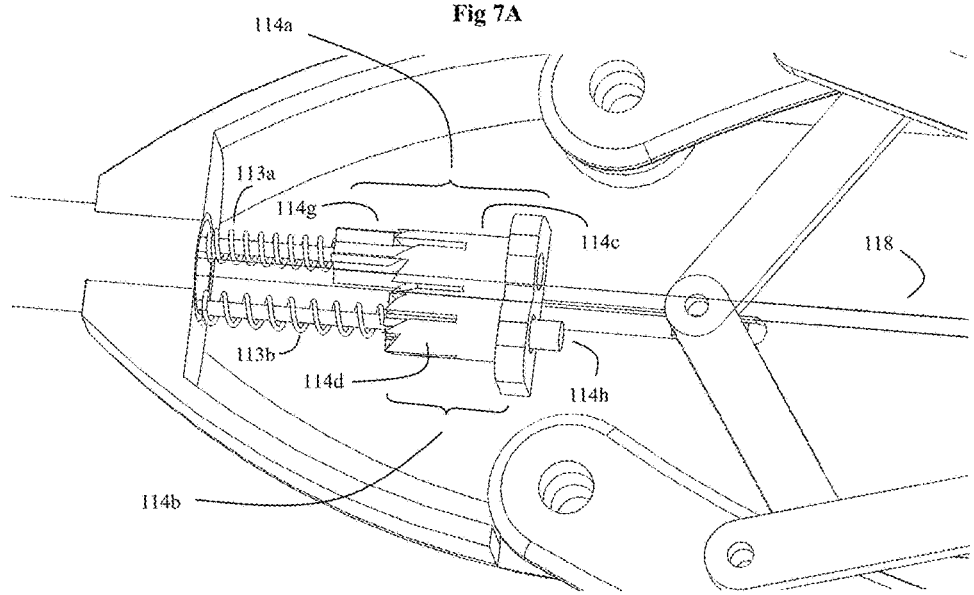
FIG. 7A shows a close up of the invention's click cam arrangement, showing a wireframe of how the dual hollow-cylinder cam and piston cam operates within the context of some of the other mechanical elements in the housing.

FIG. 7A shows a close up of the invention's click cam arrangement, showing a wireframe of how the two hollow-cylinder cams (114c, 114d) and two piston cams (114g, 114h) operate within the context of some of the other mechanical elements in the housing. Please also refer to FIG. 7E and FIG. 7F in the following discussion.

Note that the piston cams (or plunger cams) have their own plunger teeth or piston teeth (114i) positioned on an outer surface of the piston cam or plunger cam (114g or 114h), and these interact with the cam teeth (114e) located on a circumference of the hollow-cylinder cam (114c or 114d). The net effect is to implement a type of rachet and pawl mechanism.

Note that a spring (see FIG. 7A, 113a, 113b) will generally be acting to push the piston cam (or plunger cam) such as 114g into the hollow interior of the hollow cylinder cam (such as 114c). Depending on the relative state of rotation of the piston cam or plunger cam relative to the hollow-cylinder cam, the piston cam teeth (114i) will either fit into deep slots (114f) oriented along (e.g. parallel to) the axis of the hollow-cylinder cam (such as 114c), or the piston cam or plunger cam teeth (114i) will fit into a crevice in the sawtooth like cam teeth (114e) oriented along the circumference of the hollow-cylinder cam). When the plunger or piston (114c 114d) is fitting into the deep slots, the plunger or piston retracts further away from the jaw rods (112a, 112b), thus transmitting any of an opening or closing force to the jaws (104a, 104b). Thus, with every press, the piston cam or plunger cam alternates between fitting deep into the slots (114f), and fitting into the higher crevices (114e) in the saw tooth like cam teeth mounted along the circumference of the hollow cylinder cam.

Figure 7B:
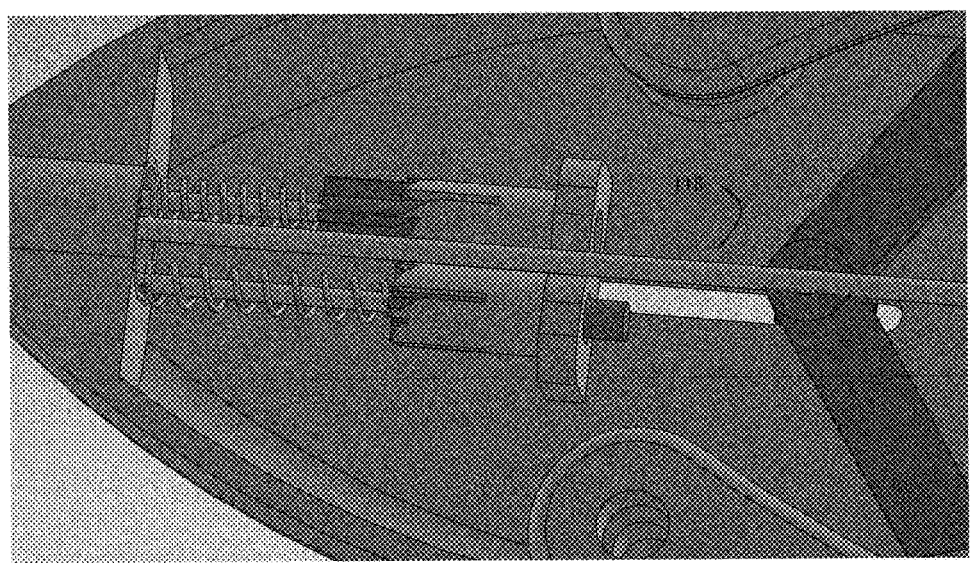
FIG. 7B shows a solid model of the click cam arrangement in the same context.

FIG. 7B shows a solid model of the click cam arrangement in the same context.

Figure 7C:
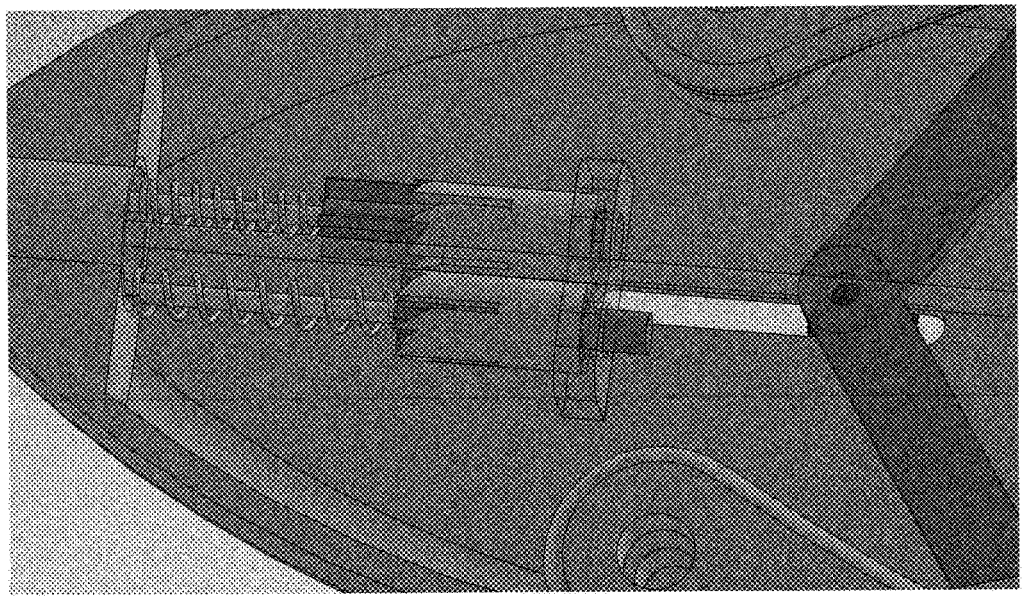
FIG. 7C shows a solid model of the click cam arrangement with some of the other mechanical elements removed.

FIG. 7C shows a solid model of the click cam arrangement with some of the other mechanical elements removed.

Figure 7D:
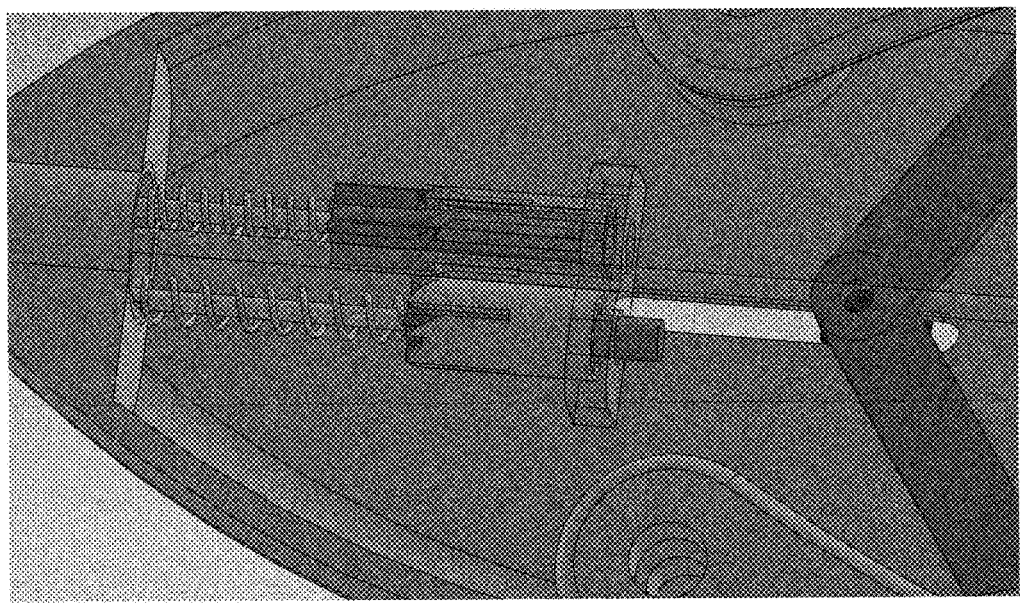
FIG. 7D shows a solid model of the click cam arrangement with one of the hollow cylindrical cams made partially transparent in order to show the inner piston cam in context.

FIG. 7D shows a solid model of the click cam arrangement with one of the hollow cylindrical cams made partially transparent in order to show the inner piston cam in context.

Figure 7E:
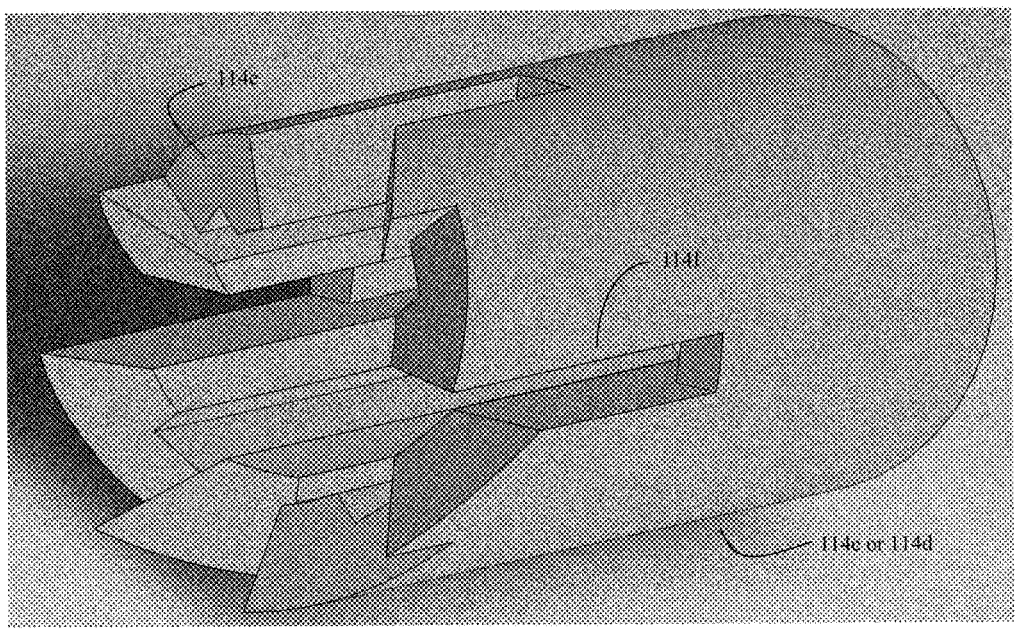
FIG. 7E shows a solid model of the hollow cylinder cam.

FIG. 7E shows a solid model of the hollow cylinder cam (114c or 114d).

Figure 7F:
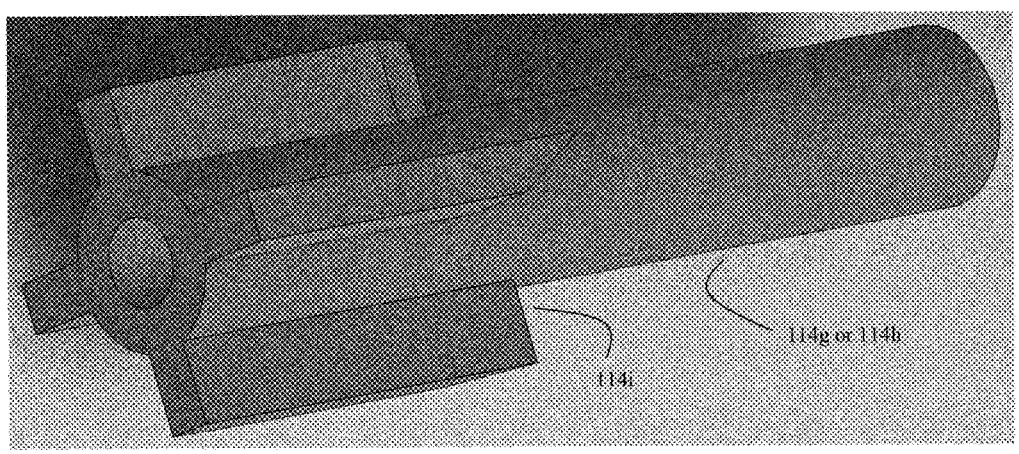
FIG. 7F shows a solid model of the piston cam, in roughly the same orientation as the hollow cylinder cam previously shown in FIG. 7E.

FIG. 7F shows a solid model of the piston cam (114g or 114h), in roughly the same orientation as the hollow cylinder cam previously shown in FIG. 7E.

Figure 7G:
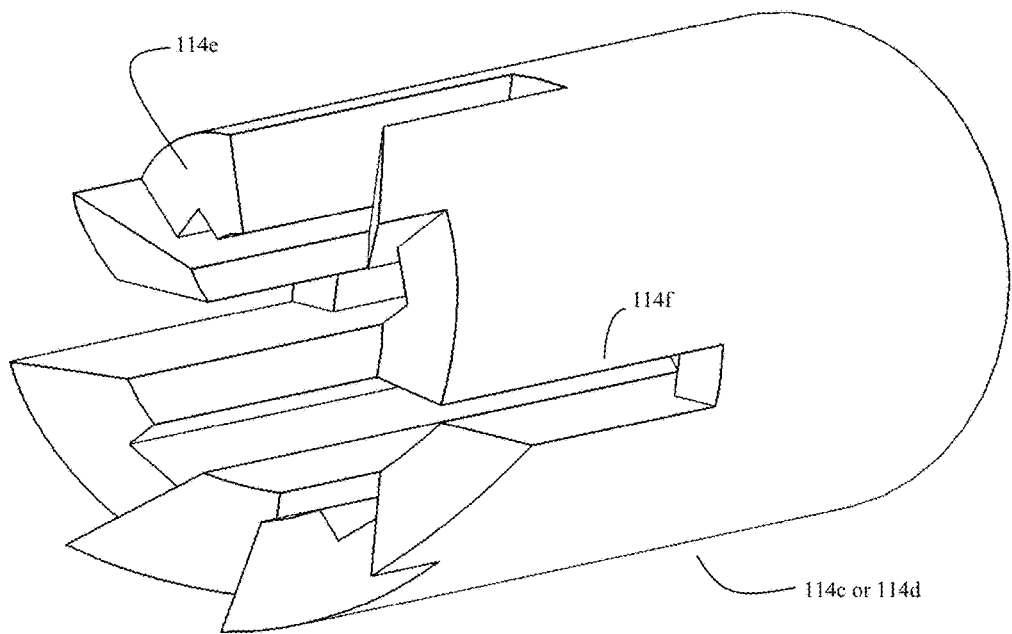
FIG. 7G shows a wireframe model of the hollow cylinder cam previously shown in FIG. 7E.
Figure 7H:
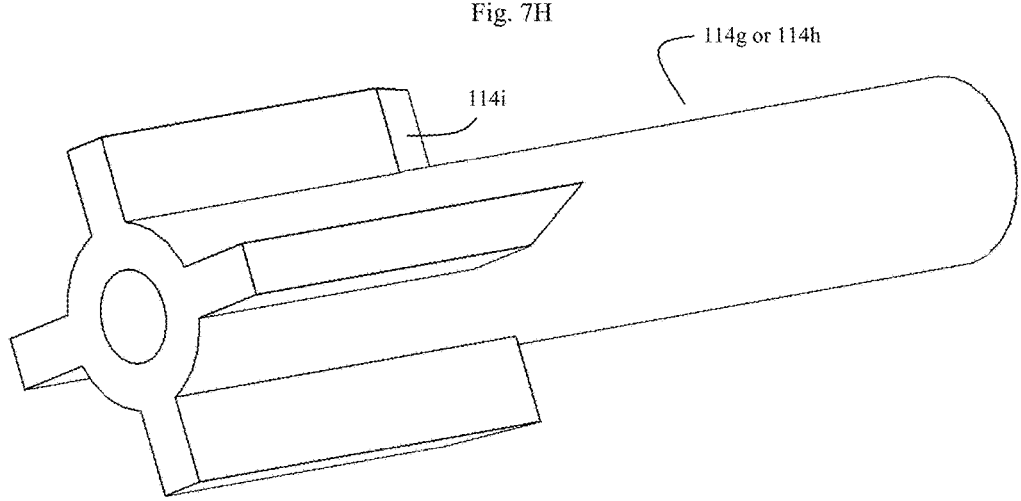
FIG. 7H shows a wireframe model of the piston cam previously shown in FIG. 7F.

FIG. 7G shows a wireframe model of the hollow cylinder cam (114c or 114d) previously shown in FIG. 7E. Note that the cam comprises various teeth, not unlike saw teeth, where generally the teeth are straight in the axial direction (114f), and sloped in the radial direction (114e). Further discussion of such cam arrangements can be found in U.S. Pat. Nos. 3,289,638; 4,991,988; and 5,263,786; the entire contents of which are incorporated herein by reference FIG. 7H shows a wireframe model of the piston cam (114g or 114h) previously shown in FIG. 7F.

Figure 8A:
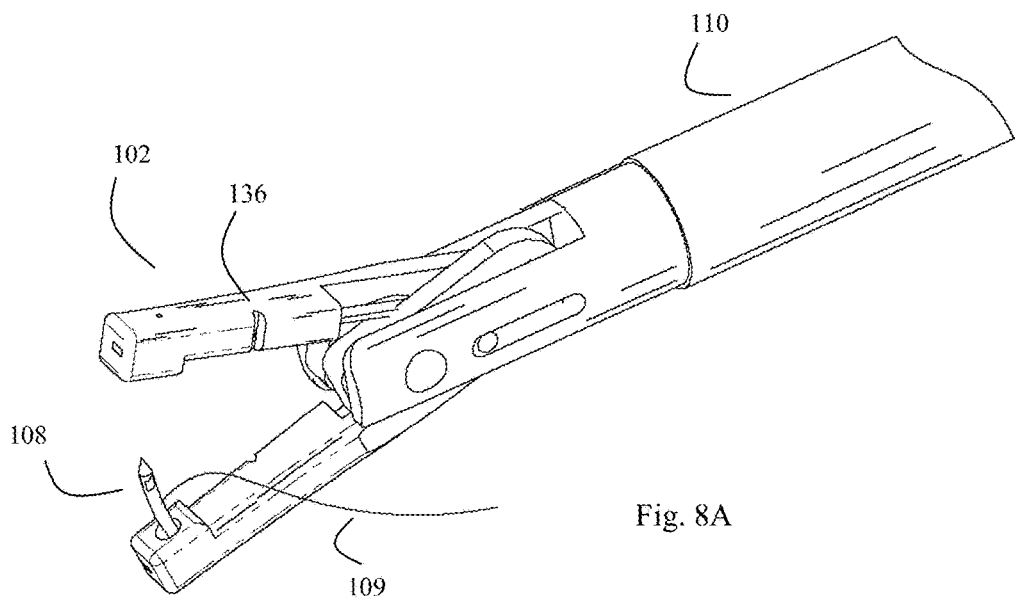
FIG. 8A shows a close-up of the device's jaw mechanism showing that in some embodiments, the device may also comprise at least one suture cutting slot mounted on at least one jaw.

FIG. 8A shows a close-up of the device's jaw mechanism (102) showing that in some embodiments, the device may also comprise at least one suture cutting slot (136) mounted on at least one jaw. Here the suture thread is also shown (109), affixed to approximately the center of the curved needle (108).

Figure 8B:
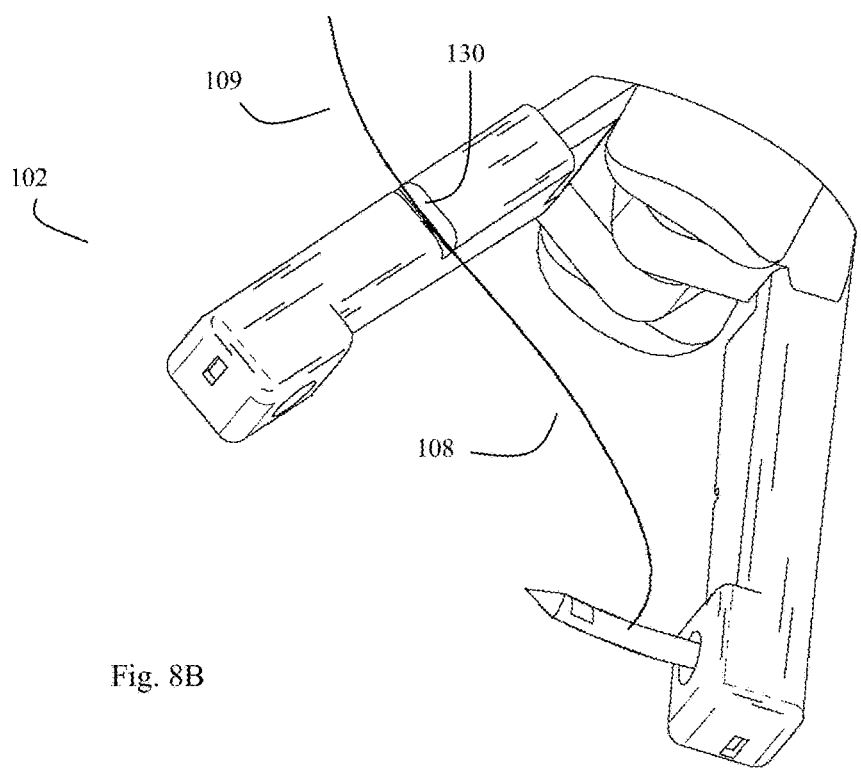
FIG. 8B shows a close-up of the device's jaw mechanism showing the suture thread aligned with a suture cutting slot.

FIG. 8B shows a close-up of the device's jaw mechanism (102) showing the suture thread (109) aligned with the suture cutting slot (136).

Figure 9A:
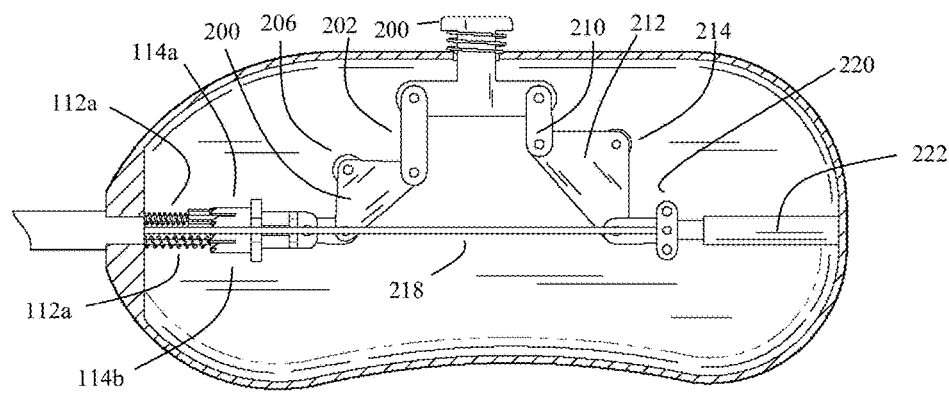
FIG. 9A shows one alternative embodiment of a housing and spring loaded mechanism arrangement.

FIG. 9A shows one alternative embodiment of a housing and spring-loaded mechanism arrangement. In this interior view of this embodiment, the spring-loaded mechanism comprises the previously discussed click cams and the device is configured to operate by an alternative push button mechanism. Here this alternative push button mechanism also forms the same human activated mechanical control mechanism used to open and shut the jaws and to produce a locking status change in both the jaw's reversibly lockable needle end openings.

In FIG. 9A, the click cam assembly (114a, 114b) which drives the locking rods, and the locking rods (112a and 112b), are driven by a different mechanism. Here a push button jaw control switch (200) is connected, via a different type of locking rod linkage (202), to a needle locking rod control pivot structure (204), which may be generally triangular. This control pivot structure (204) pivots around fixed pivot pin (206) and is connected to the click cam assembly (114a, 114b) and the locking rods (112a, 112b) in this manner.

The push button jaw control switch (200) is also connected, via jaw control linkage (210), to jaw control pivot structure (212), which may also have a generally triangular configuration. Jaw control pivot structure (212) pivots about fixed pivot pin (214), and is in turn connected to the alternate jaw control rods (218), the alternate jaw control linkage (220), and the alternate jaw control spring assembly (222) is used to normally keep the jaws (102) open in the absence of force applied to the control switch (200). The mechanism otherwise operates in a similar manner to FIG. 5.

Figure 9B:
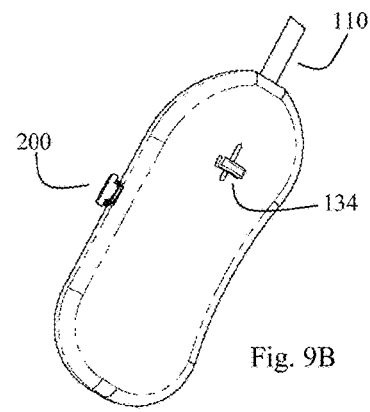
FIG. 9B shows an exterior view of the push button release configuration previously shown in FIG. 9.

FIG. 9B shows an exterior view of the push button release configuration previously shown in FIG. 9A.

Figure 10A:
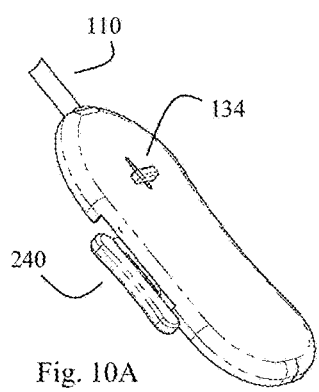
FIG. 10A shows a different exterior view of an alternative slide switch embodiment of a housing and spring-loaded mechanism arrangement.
Figure 10B:
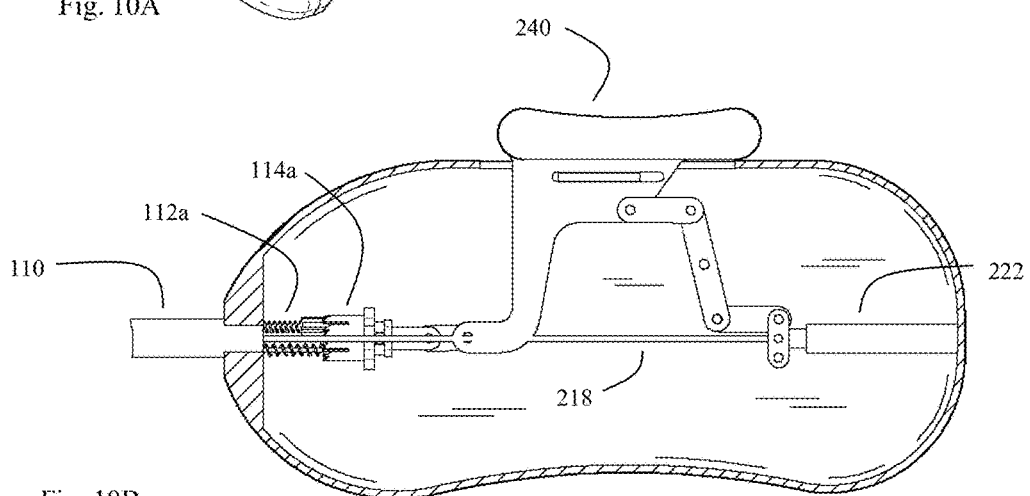
FIG. 10B shows an interior view of this slide switch configuration previously shown in FIG. 10A.

FIG. 10B shows a different interior view of an alternative slide switch (240) embodiment of a housing and spring-loaded mechanism arrangement. Here this alternative slide switch mechanism also forms a "same human activated mechanical control mechanism" used to both open and shut the jaws and produce a locking status change in both said jaw's reversibly lockable needle end openings.

In some embodiments, it is useful to configure the device to produce an audible "click" sound that confirms when the upper and lower jaws holding the needle close, and/or when each stitch has passed through tissue. Various systems and methods can be employed to produce such a "click" sound. In some embodiments, the needle locking mechanism can be configured to produce this sound by mechanical means whenever the jaws close. Here, the invention's spring loaded click cam mechanism will produce such a "click" inherently whenever it is activated.

In other embodiments, electrical sensors and suitable electrical circuitry, such as a battery, optional computer processor, and electrical audio transducer (e.g. a speaker) can be used to detect when the stitch passes through tissue. Here, for example, the jaws may be configured with sonic or ultrasonic transducers and detectors configured to vibrate the needle, as well as to detect vibration of the needle. As the needle passes through tissue, the intensity or frequency of this vibration will change, and this change in vibration can signal when the needle is passing through tissue.

Alternative electronic or optical sensing methods may also be used. In some embodiments, the needle and jaws may be configured with suitable microelectrodes and electrical impedance sensing circuitry as per the methods of Park et. al., "*Biopsy Needle Integrated with Electrical Impedance Sensing Microelectrode Array towards Realtime Needle Guidance and Tissue Discrimination*", Nature scientific reports (2018) 8:264 DOI:10.1038/s41598-017-18360-4. Alternatively, in some embodiments, the needle itself may be configured with suitable optical sensors, which in turn can connect to optical detectors, light sources, or optical fiber cables in the jaws, and needle passing through tissue detected as per the methods of Anderson et. al., PCT patent publication WO 2015/200712, the entire contents of which are incorporated herein by reference.

The electrical circuitry (e.g. a computer processor) can be configured to produce an audible signal when the needle is passing through tissue. Such audible feedback can help users use the device more accurately. Thus, according to the invention, the apparatus will often produce an audible signal whenever the needle changes its state. In addition to the natural "click" produced by the invention's click cam mechanism as the needle is transferred from one jaw to the other jaw, additional audio sounds may optionally also be produced when the apparatus detects that the needle is in the state of passing through tissue.

FIG. 10A shows an exterior view of this slide switch configuration previously shown in FIG. 10B.

Figure 10C:
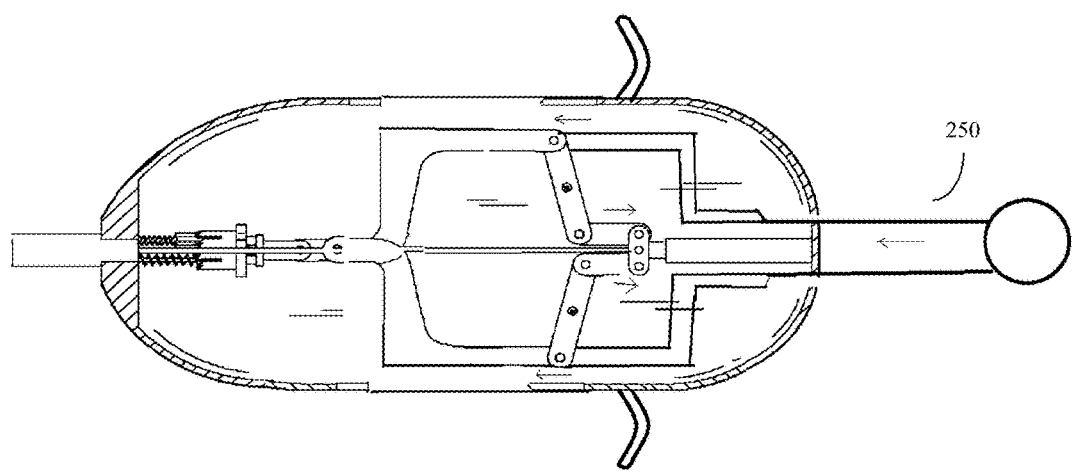
FIG. 10C shows an alternative embodiment of the device, in which the functionality of the side switch or button is instead implemented by a "syringe handle" (e.g. a moving control piston) type configuration.

As will be discussed, other types slide switches or "human activated mechanical control mechanisms" can also be used. For example, FIG. 10C shows an example of a control piston type slide switch, in which a human operator opens and shuts the valves by pushing or pulling on a control piston arrangement (250).

Figure 11:
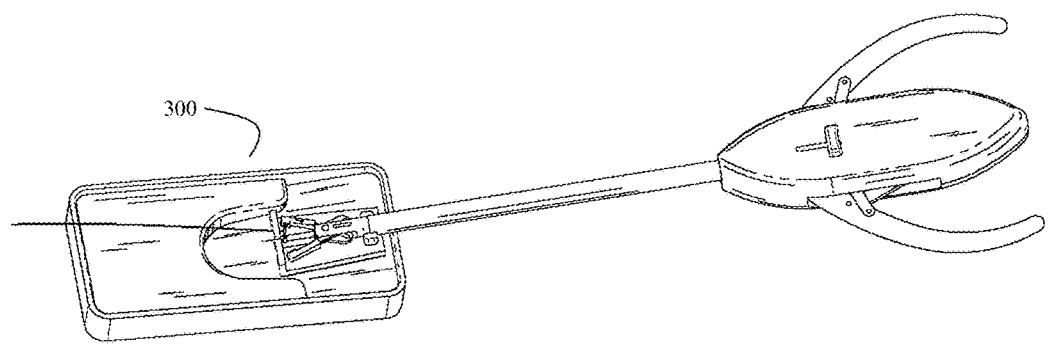
FIG. 11 shows a close-up view of the needle loading cartridge, which can be used to provide a sterilized needle and attached suture thread to the device's jaw assembly.

FIG. 11 shows a close-up view of a needle loading cartridge device (300) that can be used to provide a sterilized needle and attached suture thread to the device's jaw assembly. Here, designs such as taught by Kirsch, US patent application 2010/0262165, the contents of which are incorporated herein by reference, may be used. Alternative designs may also be used.

Figure 12:
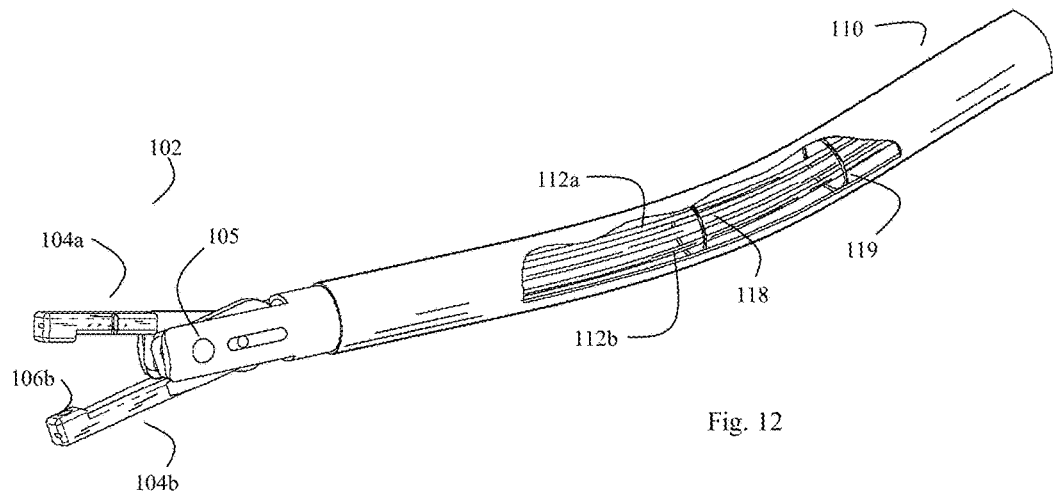
FIG. 12 shows a detail of the inside of the device's substantially hollow shaft, showing the first and second locking rods, and optional rod stabilizer rings that can be used to prevent the rods from buckling when the shaft is bent.

FIG. 12 shows a detail of the inside of the device's substantially hollow shaft (110), showing the first and second locking rods (112a, 112b), jaw open-shut control rod (118) and optional rod stabilizer rings (119) that can be used to prevent the rods from buckling when the shaft is bent. Additional details of the jaw mechanism (102) comprising two jaws (104a, 104b) can also be seen. The two jaws rotate or pivot about a jaw pivot (105) and open and shut in response to force applied by the jaw open-shut control rod (118). Details of the reversibly lockable needle end openings (106b), (106a is hidden) are also shown.

Figure 13:
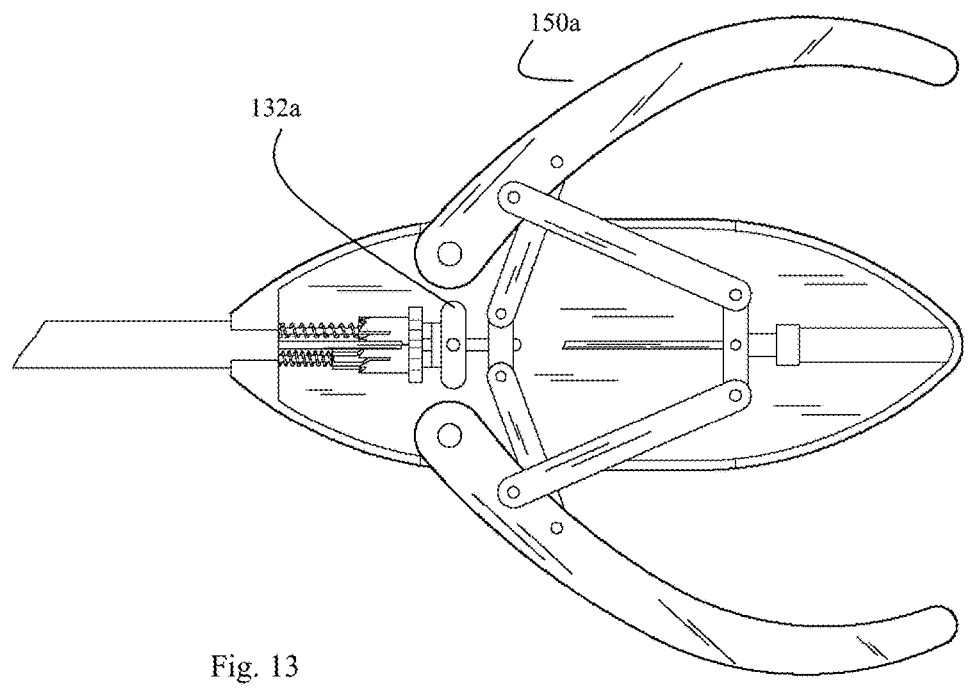
FIG. 13 shows an example of a needle quick release override switch that does not require that the handles be depressed in order to release the needle.

FIG. 13 shows an example of a needle quick release override control mechanism (132a, 132b) that works in conjunction with needle release override switch (134). This override system can release the needle regardless of the status of the control handles (150a, 150b) or other control mechanisms such as (200, or 240).

Figure 14:
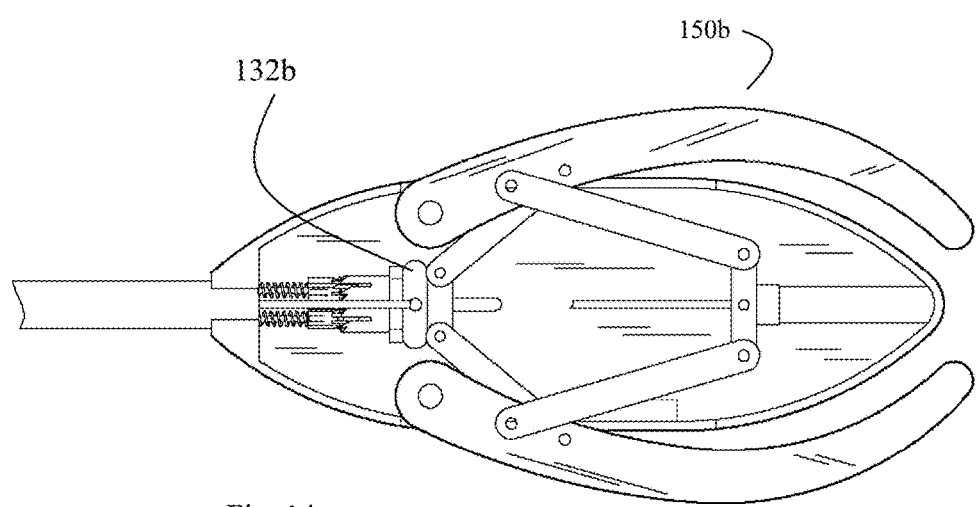
FIG. 14 shows an example of how the override witch slides along with the handles under normal use.

FIG. 14 shows an example of how the override mechanism (132a, 132b) slides along with the control handles (150a, 150b) under normal use. However, by engaging slide switch (134), the override mechanism (132a, 132b) can be operated independently of the control handles.

Figure 15:
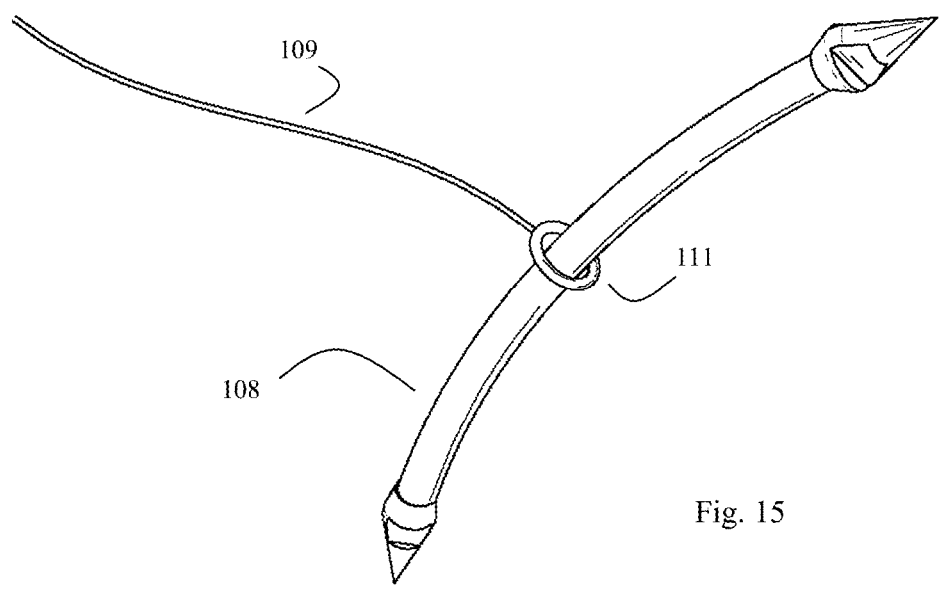
FIG. 15 shows an alternative "sliding ring" suture thread attachment to the device's curved needle, which may result in less tissue drag relative to prior art fixed suture attachment art.

FIG. 15 shows an alternative "sliding ring" (111) suture thread (109) attachment to the device's curved needle (108), which may result in less tissue drag relative to prior art fixed suture to needle attachment art.

Figure 16A:
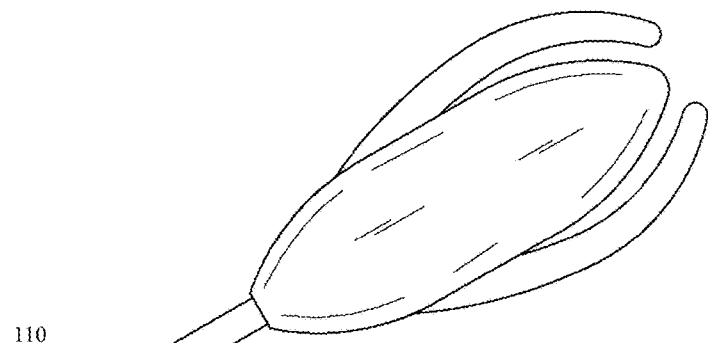
FIGS. 16A, 16B, and 16C show how the device may be used in open small deep suture applications.
Figure 16B:
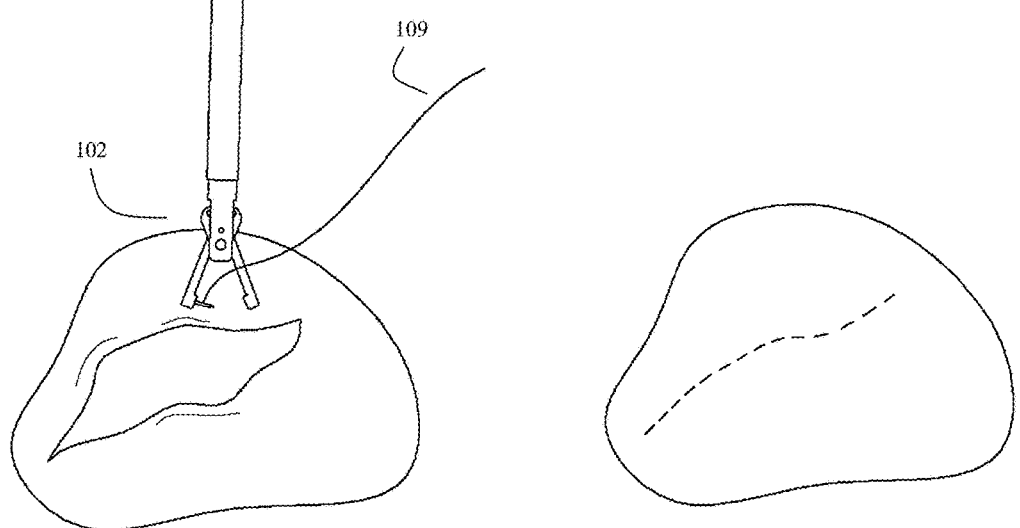
Figure 16C:
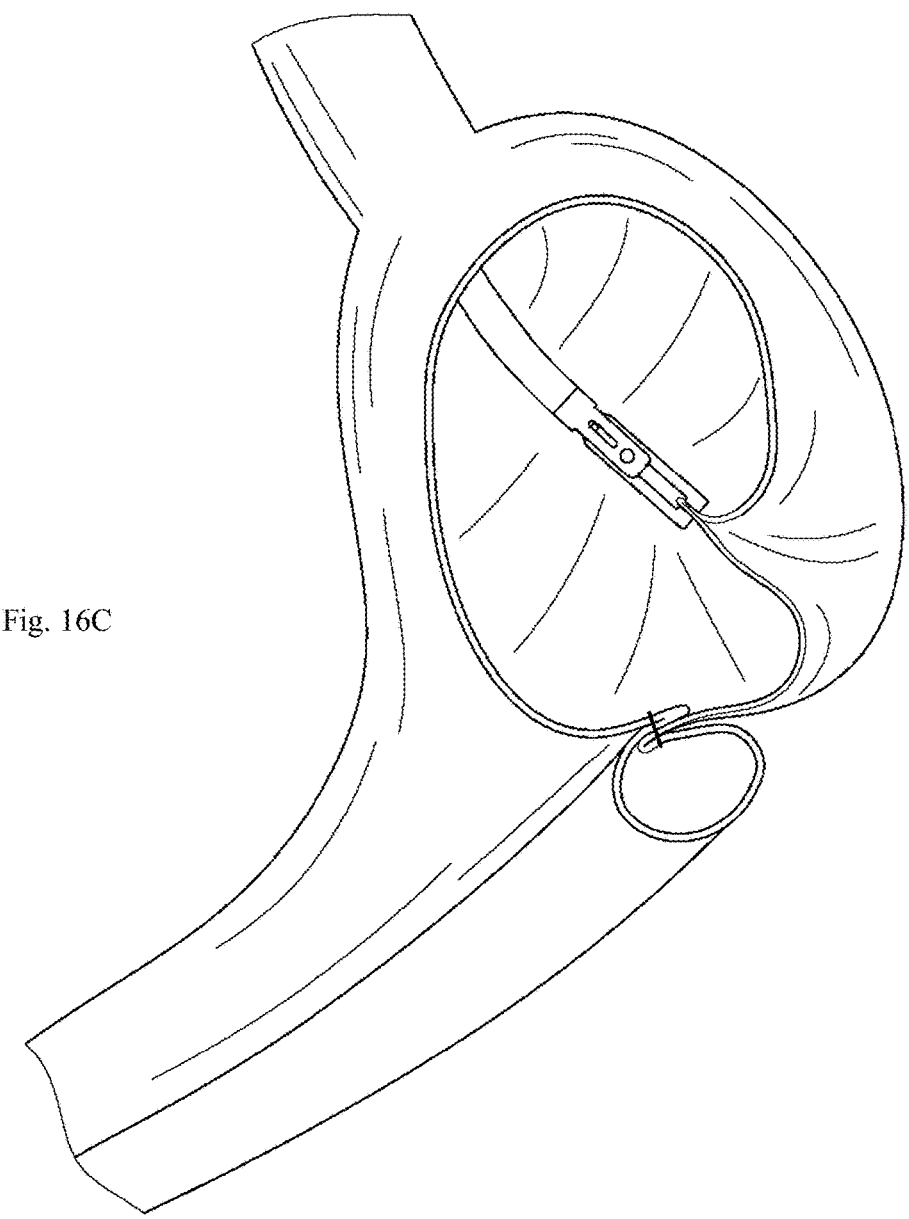

FIGS. 16A, 16B, and 16C show how the device may be used in open small deep suture applications. These applications include cardiothoracic applications such as—Mitral valve leaflet repair, other intra cardiac repairs, septal defects, and great vessel repairs. Other applications include urology applications such as Nephrectomy—deep surgical cavity sutures, Gynecology—pelvic floor repair (e.g. to attach mesh to the pelvic floor), Vascular—Carotid Endarterectomy small vessel repair, General surgery—Thyroidectomy, Fem-POP, inguinal hernia repair, and other types of small incision tissue repairs.

Figure 17A:
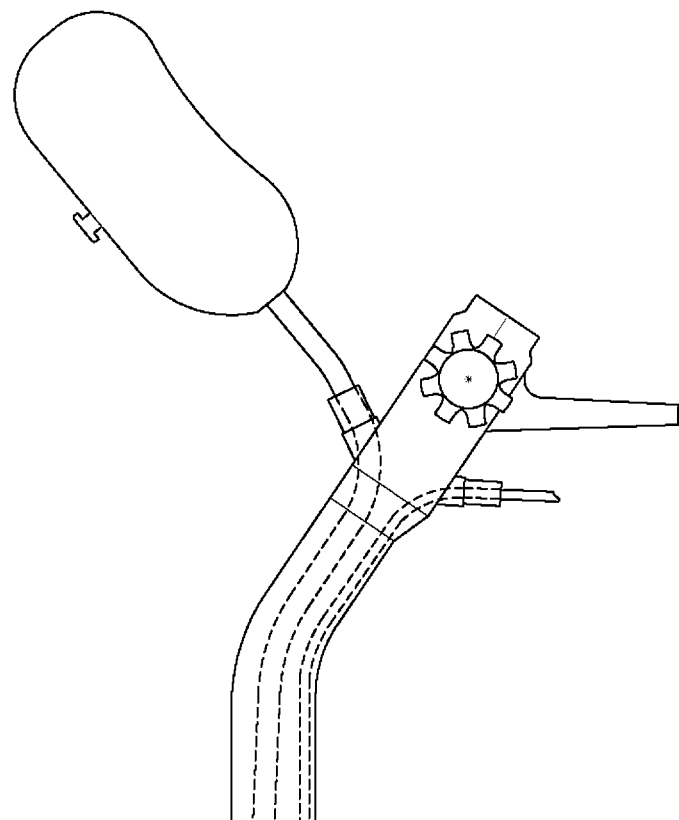
FIG. 17A shows use of the invention for endoscopic surgery.
Figure 17A:
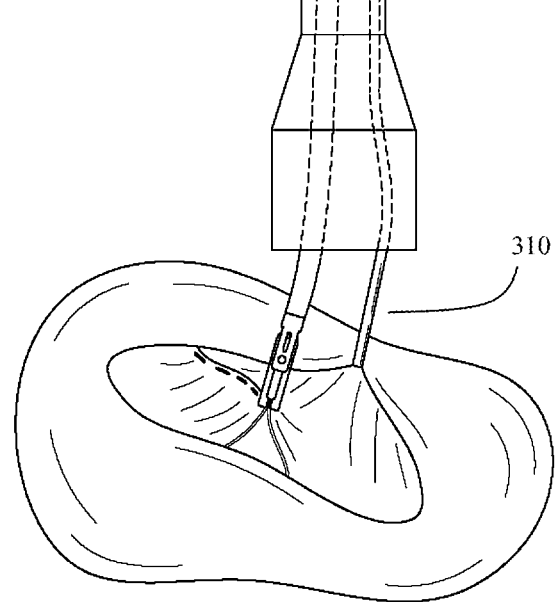

FIG. 17A shows use of the invention for endoscopic surgery. Here the invention, sometimes in the push button and/or slide button configuration, may be used with a flexible scope. In this embodiment, the jaws may be attached after the shaft is passed thru the scope. In this drawing, note that a suction tube (310 is being used to retract tissue into the invention's jaws. This technique enables perpendicular tissue suturing.

Procedure examples are: Bariatric—Natural orifice gastric cosmetic surgery, Gastrointestinal—Gastro intestinal lesion repair and Natural orifice transluminal endoscopic surgical procedures, Interventional Radiology—Transvaginal hybrid natural orifice transluminal endoscopic surgery, and the like.

Figure 17B:
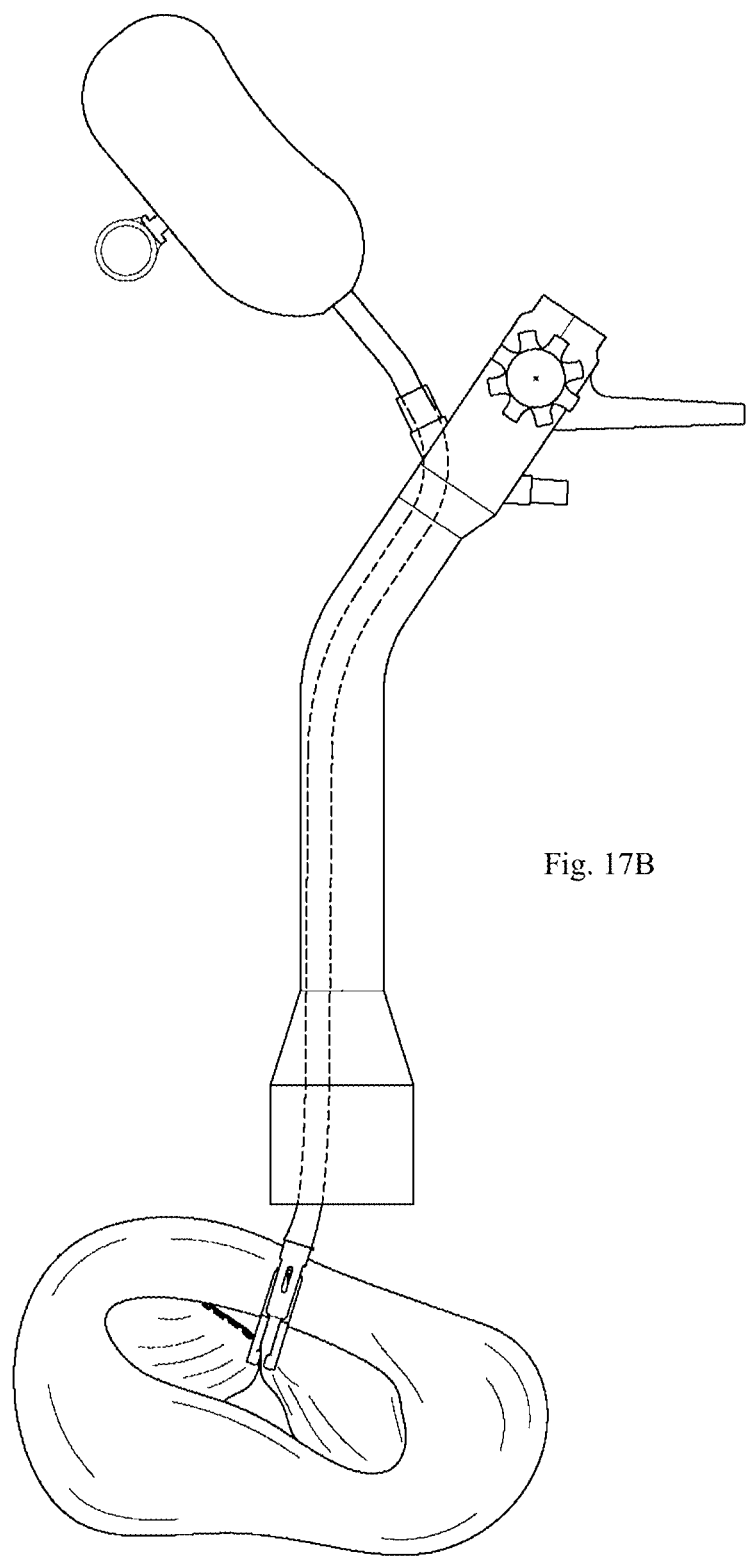
FIG. 17B shows a "single channel" endoscope embodiment of the invention, configured to suture tissue without the aid of additional tissue positioning lines placed in the endoscope.

FIG. 17B shows an alternative embodiment in which the invention is configured for use in a "single channel" or single line endoscope embodiment. This single channel or single line endoscope embodiment can be used with a single channel or single line endoscope that may, for example, not require use of an additional suction tube (310) or other separate endoscopic positioning "line" to retract tissue into the invention's jaws.

To enable the invention to better perform in this "single channel" (no separate positioning tube or line) embodiment, the invention's jaws can be configured to articulate to an alternative "wide open jaw" position. When the invention is positioned in a perpendicular plane with respect to the tissue, this wide-open jaw configuration allows the needle to pierce the tissue, without requiring the need for the tissue to be retracted with another instrument, such as suction tube (310) or other tissue positioning device. This is shown in FIGS. 17C, 17D and 17E.

Figure 17C:
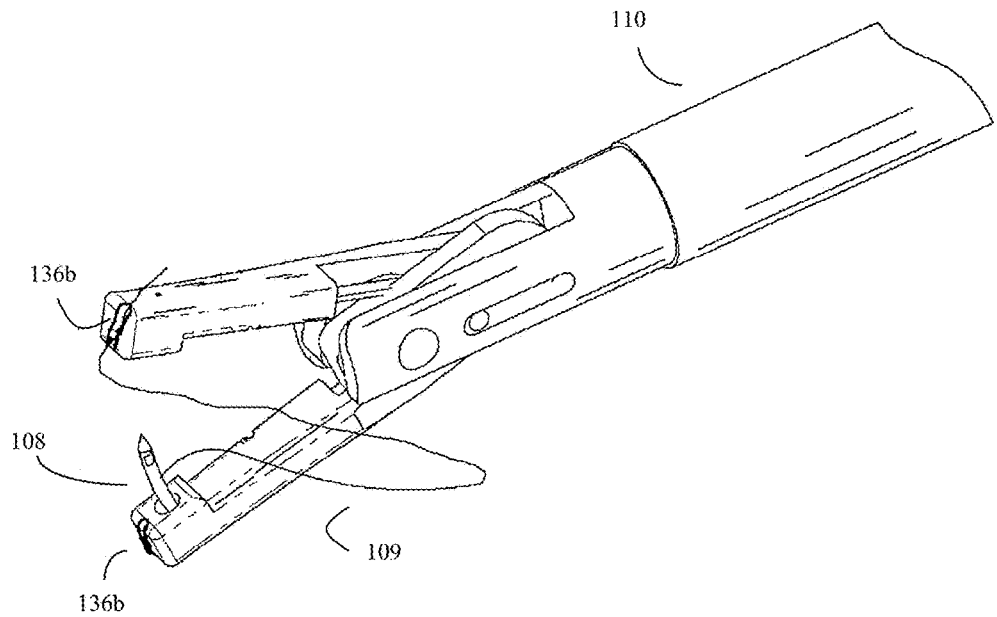
FIG. 17C shows an alternative configuration where the cutting slot or blade is positioned at the extreme distal end of the jaw.
Figure 17D:
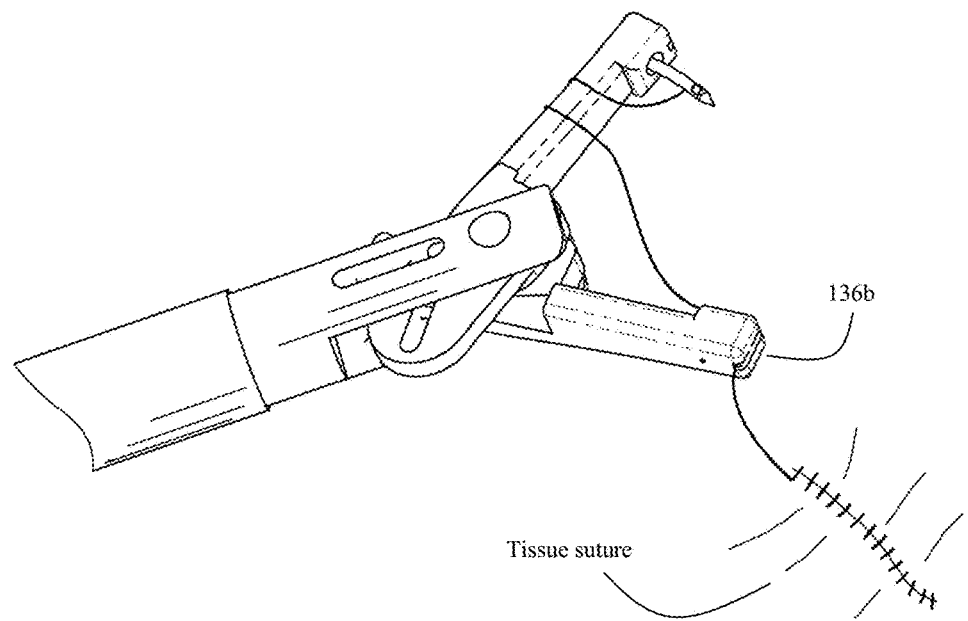
FIG. 17D shows how by positioning the cutting slot or blade at the extreme distal end of the jaw, the jaw may be positioned more closely to the tissue suture.

FIG. 17C shows that in this alternative jaw embodiment, the position of the cutting slot or blade (136) can be reoriented to an alternative location (136b) on the distal portion of the jaws. As desired, the original cutting slot (136) may either be removed from its' original location, or alternatively cutting slots may be put in both positions. The location of cutting slot (136b) is useful because allows the cutter (cutting slot 136b) to now be oriented very close to the location of a suture knot on the perpendicular plane. This is shown in FIG. 17D and FIG. 17E.

This allows the invention's jaw to now operate as a more efficient "cutting jaw", allowing the jaw to operate very close to the suture knot. This leaves a very small tail on the knot, and makes it more feasible to operate without additional tissue positioning devices such as suction tube (310).

Figure 17E:
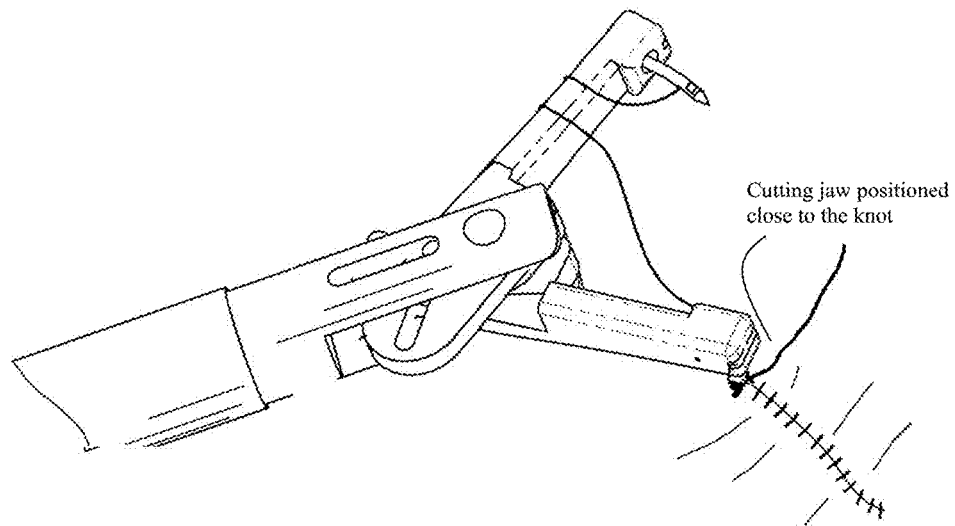
FIG. 17E shows how by positioning the cutting slot or blade at the extreme distal end of the jaw, the "cutting jaw" may be brought extremely close to the suture knot, thus producing a very small tail of remaining suture line after the knot.

In this alternative embodiment, upon completion of tissue suturing, the jaws are opened and any excess suture is coiled onto the jaw as shown in FIG. 17E. By positioning the cutting slot or blade on the extreme distal end of the jaws, this alternative embodiment enables the cutting slot (136b) in a position to cut extremely close to the suture knot. This reduces the excess suture knot tail, which is desirable because an excess knot tail can interfere with the surrounding tissue and anatomy.

Figure 17F:
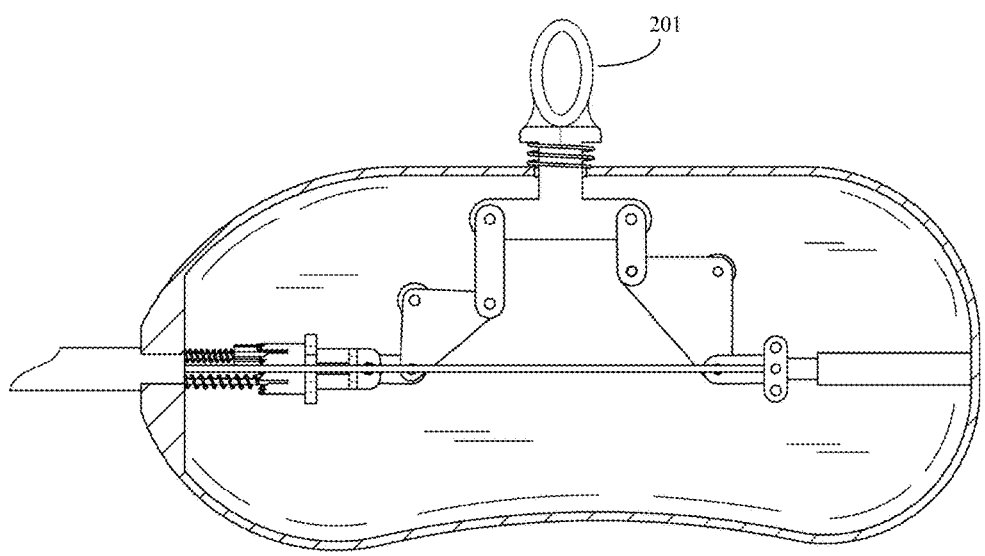
FIG. 17F shows how an alternative embodiment of FIG. 9A, here with a thumb ring mounted on the control knob to facilitate more extensive jaw position manipulation.

In some embodiments, as is shown in FIG. 17F, to facilitate the greater jaw manipulation required under this "no additional tissue positioning devices" mode (or even for normal mode with positioning devices), a thumb ring (201) may be placed on top of the control knob (200) to facilitate better jaw manipulation. This control knob can help supplement the action of the control knob return spring, and allow the user to apply additional force to open and close the jaws to a wider extent.

Figure 18C:
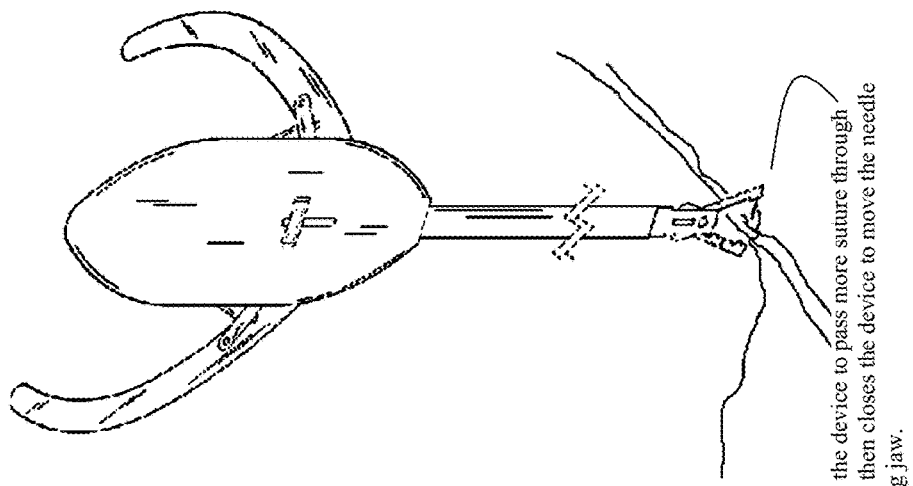
FIG. 18C shows that after the needle and suture have based through both tissue sections of the incision, the operator can then pull the device to pass more of the suture through the small needle hole in the tissue. The operator can then close the device's jaws, which according to the invention also transfers the needle from the first jaw to an opposite jaw. The operator can then repeat this sequence of steps to create a running stitch.
Figure 18B:
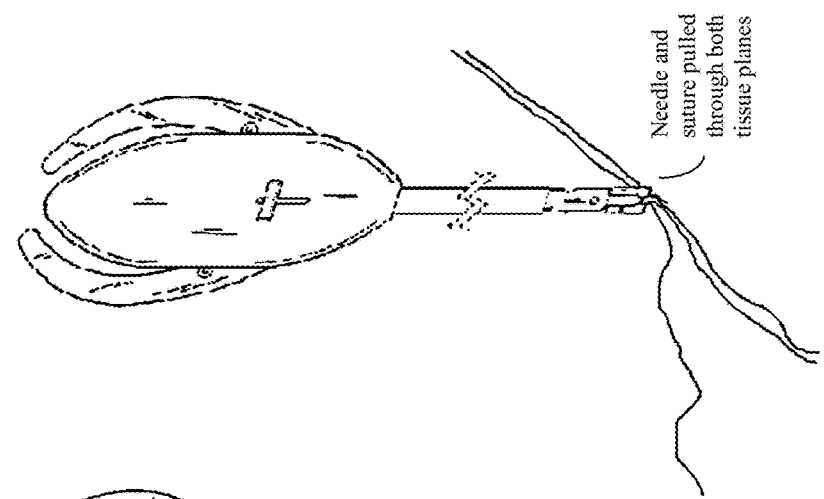
FIG. 18B shows the needle and suture immediately after they have been passed through both tissue sections (e.g. planes) of the incision.
Figure 18A:
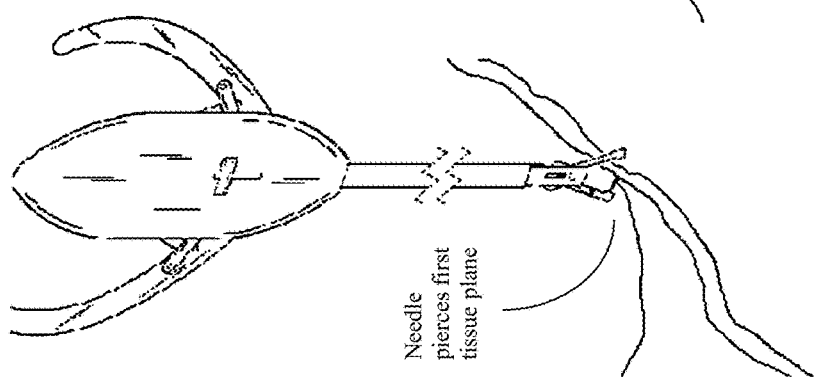
FIG. 18A shows an example of how the invention can be used to produce running stitches. Here the needle is shown piercing a first tissue plane (e.g. tissue section) of an incision (with two adjacent tissue sections).

FIG. 18A to FIG. 18C shows an example of how the invention can be used to produce running stitches.

In FIG. 18A, the needle is shown piercing a first tissue plane of an incision (with two adjacent tissue planes). FIG. 18B shows the needle and suture immediately after they have been passed through both tissue planes of the incision. FIG. 18C shows that after the needle and suture have based through both tissue planes of the incision, the operator can then pull the device to pass more of the suture through the small needle hole spanning the two tissue planes. The operator can then close the device's jaws, which according to the invention also transfers the needle from the first jaw to an opposite jaw. The operator can then repeat this sequence of steps to create a running stitch.

Other Embodiments

In some embodiments, the invention may be an apparatus and a method for surgical suturing with thread management. An illustrative apparatus for tissue suturing includes a cartridge having a curved suturing needle having pointed ends and a hinge in the center with suture attached to the hinge, the suturing needle capable of oscillating about an axis, a reciprocating needle drive, with jaws capable of releasably engaging the needle. A method for suturing tissue is provided that includes placing a suturing device having dual spring-loaded triangular cams that tilts from side to side thereby activating 2 shafts to automatically lock and release said needle from one jaw to the other jaw to span at least one tissue segment, activating the cams by closing control handle assembly to cause movement of the suturing needle through at least one tissue segment, and stop an advancing movement of the suturing needle to cause a suturing material to be pulled through the at least one tissue segment forming a stitch.

For example, the invention may also be an apparatus for operating on tissue, the apparatus comprising: (a) a jaw apparatus housing defining two jaws with openings, wherein the jaws are configured to receive a curved needle such that the needle is movable within the two openings, wherein the openings with guide channels are arcuate; (b) a rod assembly positioned proximate to the needle within the openings, wherein the rod assembly is translatable relative to the housing wherein the rod assembly comprises: (i) a spring-loaded triangular cam at proximal end of both rods, and (ii) wherein the spring-loaded triangular cams independently moves the two rod assemblies longitudinally within the jaw apparatus housing, wherein the rod assembly lock and unlock needle from jaw to jaw wherein the spring-loaded triangular cam assemblies are activated when attached control handle is in the close position. One rod assembly is configured to engage the needle in the lock position when second rod assembly is configured to disengage the needle in the unlock position; and (c) a needle driver coupled with the spring loaded triangular cam rod assembly, wherein the needle driver is configured to engage the needle to thereby cause lock and release of needle via jaws causing bidirectional movement of needle thru tissue from jaw to jaw, needle travels half the length of the needle within the jaws.

In some embodiments, the first jaw opening leads to a curved channel within the opening to receive the needle. Some embodiments may also comprise a second jaw wherein the opening leads to a curved channel within opening to receive the needle.

In some embodiments, the operator portion of the housing may comprise a spring-loaded triangular cam assembly attached to first-rod assembly. The operator portion of the housing may also comprise a second spring-loaded triangular cam assembly attached to a second-rod assembly. Here, the movement of dual rod assemblies may be independently activated by a control handle assembly, located on the operator portion of the housing in the closed position. Further, the apparatus may also comprise a needle driver comprising a dual rod assembly configured to extend through the channel of the jaw portion of the housing, wherein the dual rod assembly is configured to engage the needle.

In this configuration, the needle driver may further comprises a first jaw with a notch in the distil tip with one or more cutting blades fixed to the notch. This first jaw can be guided to suture via this notch blade to cut the suture when needed. The needle driver can be further configured to perform a complete stitch with a single hand motion without activating additional levers or switches.

In some embodiments, the apparatus may further comprise third and four sliding levers to activate rod assemblies in the closed position. Typically, the jaw portion of the housing is configured to receive tissue, within jaws wherein the apparatus is configured to suture the tissue received within the jaws. The needle is typically a curved suturing needle having pointed ends and a hinge in the center with suture attached to the hinge, thereby limiting tissue irritation of suture drag.

In some embodiments, the shaft may also comprise strategically placed guide washers to maintain longitudinal alignment of the rod assemblies and cable for jaw movement. The shaft and rod assemblies may, if desired, be further comprised of a malleable material to facilitate an adjustable shaft for jaw orientation to tissue. In some embodiments, some or all of the shaft assembly may be comprised of flexible material to facilitate operation via a flexible scope working channel for endoscopic surgical procedures.

The invention claimed is:

1. An apparatus for suturing tissue, said apparatus comprising:
    a jaw mechanism comprising two pivoting jaws, each jaw comprising reversibly lockable needle end openings, both said jaws configured to receive a curved needle such that said curved needle is movable within and between said reversibly lockable needle end openings, said jaw mechanism positioned on a distal end of a substantially hollow shaft;
    a housing comprising at least one spring loaded click cam mechanism, said housing positioned at a proximal end of said substantially hollow shaft
    said at least one spring loaded click cam mechanisms configured to automatically use a same human activated mechanical control mechanism to both open and shut said jaws and produce a locking status change in both said jaw's reversibly lockable needle end openings;
    said locking status change comprising a change from a locked to an unlocked status for one said jaw, and a change from an unlocked to a locked status for the other said jaw, each said jaw being in a different locking status.

2. The apparatus of claim 1, further comprising a locking rod assembly comprising a first and second locking rod, portions of said locking rod assembly being positioned proximate to said jaw mechanism, portions of said locking rod assembly configured to reside inside said substantially hollow shaft and to be translatable relative to said substantially hollow shaft.

3. The apparatus of claim 2, wherein said housing is further configured to receive proximal portions of said first and second locking rods; and
    said at least one spring loaded click cam mechanisms further configured for independent movement of said first and second locking rods longitudinally within said housing and said substantially hollow shaft.

4. The apparatus of claim 1, wherein said at least one spring loaded click cam mechanism comprises a hollow cylindrical cam and piston cam arrangement; and
    wherein said hollow cylindrical cam is configured to rotate with respect to said piston cam; or wherein said piston cam arrangement is configured to rotate with respect to said hollow cylindrical cam.

5. An apparatus for suturing tissue, said apparatus comprising:
    a jaw mechanism comprising two pivoting jaws, each jaw comprising reversibly lockable needle end openings, both said jaws configured to receive a curved needle such that said curved needle is movable within and between said reversibly lockable needle end openings, said jaw mechanism positioned on a distal end of a substantially hollow shaft;
    a locking rod assembly comprising a first and second locking rod, portions of said locking rod assembly being positioned proximate to said jaw mechanism, portions of said locking rod assembly configured to reside inside said substantially hollow shaft and to be translatable relative to said substantially hollow shaft;
    a housing comprising at least one spring loaded click cam mechanism, said housing positioned at a proximal end of said substantially hollow shaft, and configured to receive proximal portions of said first and second locking rods;
    said at least one spring loaded click cam mechanisms configured for independent movement of said first and second locking rods longitudinally within said housing and said substantially hollow shaft;
    said locking rod assembly and said at least one spring loaded click cam mechanisms configured to automatically use a same human activated mechanical control mechanism to both open and shut said jaws and produce a locking status change in both said jaw's reversibly lockable needle end openings;
    said locking status change comprising a change from a locked to an unlocked status for one said jaw, and a change from an unlocked to a locked status for the other said jaw, each said jaw being in a different locking status.

6. The apparatus of claim 5, wherein said first locking rod and said jaw mechanism is configured to engage said curved needle in a locked position on one said jaw, and another said jaw is configured to disengage said curved needle from an unlocked position on said other said jaw.

7. The apparatus of claim 5, wherein said at least one spring loaded mechanism comprises a first spring loaded triangular structure assembly attached to said first locking rod.

8. The apparatus of claim 7, wherein said at least one spring loaded mechanism further comprises a second spring loaded triangular structure assembly attached to said second locking rod.

9. The apparatus of claim 8, wherein said human activated mechanical control mechanism comprises a control handle assembly, and said movement of said first and second locking rods are independently activated by said control handle assembly.

10. The apparatus of claim 5, wherein said human activated mechanical control mechanism comprises a control piston assembly, and said movement of said first and second locking rods are independently activated by a position of said control piston in said piston assembly.

11. The apparatus of claim 5, wherein said at least one spring loaded click cam mechanism comprises a hollow cylindrical cam and piston cam arrangement.

12. The apparatus of claim 11, wherein said hollow cylindrical cam is configured to rotate with respect to said piston cam; or wherein said piston cam arrangement is configured to rotate with respect to said hollow cylindrical cam.

13. The apparatus of claim 5, wherein said at least one spring loaded click cam mechanism comprises two spring loaded click cam mechanisms, each comprising a hollow cylindrical cam and piston cam arrangement.

14. The apparatus of claim 5, wherein said human activated mechanical control mechanism comprises a control handle assembly, and said control handle assembly also controls said pivoting of said jaws between an open and a shut configuration.

15. The apparatus of claim 5, wherein said human activated mechanical control mechanism comprises a control piston assembly, and said pivoting of said jaws between an open and a shut configuration is also controlled by a position of said piston in said control piston assembly.

16. The apparatus of claim 5, wherein at least one of said jaws has at least one suture cutting slot to facilitate cutting of suture, said at least one suture cutting slot being positioned on any of a side of said jaw or an extreme distal end of said jaw.

17. The apparatus of claim 5, wherein said needle has a needle length, and wherein said suture is configured to attach to said needle so as to facilitate sliding along said needle length, thus reducing tissue drag.

18. The apparatus of claim 5, wherein said jaw mechanism is configured to be detachable from said shaft.

19. The apparatus of claim 5, wherein said apparatus is further configured to either produce or change an audible signal when a needle, reversibly attached to at least one of said jaws, changes its state.

20. An apparatus for suturing tissue, said apparatus comprising:
- a jaw mechanism comprising two pivoting jaws, each jaw comprising reversibly lockable needle end openings, both said jaws configured to receive a curved needle such that said curved needle is movable within and between said reversibly lockable needle end openings, said jaw mechanism positioned on a distal end of a substantially hollow shaft;
- a locking rod assembly comprising a first and second locking rod, portions of said locking rod assembly being positioned proximate to said jaw mechanism, portions of said locking rod assembly configured to reside inside said substantially hollow shaft and to be translatable relative to said substantially hollow shaft;
- a housing comprising a plurality of spring loaded click cam mechanisms, each comprising a hollow cylindrical cam and piston cam, said housing positioned at a proximal end of said substantially hollow shaft, and configured to receive proximal portions of said first and second locking rods;
- said plurality of spring loaded click cam mechanisms configured for independent movement of said first and second locking rods longitudinally within said housing and said substantially hollow shaft;
- said locking rod assembly and said plurality of spring loaded click cam mechanisms configured to automatically use a same human activated mechanical control mechanism to both open and shut said jaws and produce a locking status change in both said jaw's reversibly lockable needle end openings;
- said locking status change comprising a change from a locked to an unlocked status for one said jaw, and a change from an unlocked to a locked status for the other said jaw, each said jaw being in a different locking status;
- wherein said apparatus is further configured to either produce or change an audible signal when a needle, reversibly attached to at least one of said jaws, changes its state.

* * * * *